(12) United States Patent
Brown et al.

(10) Patent No.: US 9,376,529 B2
(45) Date of Patent: Jun. 28, 2016

(54) FLUORO MONOMERS, OLIGOMERS, AND POLYMERS FOR INKS AND ORGANIC ELECTRONIC DEVICES

(75) Inventors: Christopher T. Brown, Pittsburgh, PA (US); Elena E. Sheina, Pittsburgh, PA (US); Ting Xu, Pittsburgh, PA (US)

(73) Assignee: SOLVAY USA INC., Princeton, NJ (US)

( * ) Notice: Subject to any disclaimer, the term of this patent is extended or adjusted under 35 U.S.C. 154(b) by 672 days.

(21) Appl. No.: 13/326,027

(22) Filed: Dec. 14, 2011

(65) Prior Publication Data

US 2012/0152357 A1    Jun. 21, 2012

Related U.S. Application Data

(60) Provisional application No. 61/423,571, filed on Dec. 15, 2010.

(51) Int. Cl.
| | | |
|---|---|---|
| *C07D 285/14* | (2006.01) | |
| *C08G 61/12* | (2006.01) | |
| *C07D 495/04* | (2006.01) | |

(Continued)

(52) U.S. Cl.
CPC ............ *C08G 61/123* (2013.01); *C07D 285/14* (2013.01); *C07D 495/04* (2013.01); *C07D 513/04* (2013.01); *C08G 61/126* (2013.01); *C09B 57/00* (2013.01); *C09B 69/109* (2013.01); *H01L 51/0043* (2013.01); *H01L 51/4253* (2013.01); *C08G 2261/124* (2013.01); *C08G 2261/146* (2013.01); *C08G 2261/1412* (2013.01); *C08G 2261/18* (2013.01); *C08G 2261/3243* (2013.01);

(Continued)

(58) Field of Classification Search
USPC .............................. 257/40; 524/609; 548/126
See application file for complete search history.

(56) References Cited

U.S. PATENT DOCUMENTS 8,558,108 B2 * 10/2013 Kitazawa et al. .............. 136/263
2010/0252112 A1 * 10/2010 Watson ......................... 136/263

(Continued)

FOREIGN PATENT DOCUMENTS

EP           2266982 A1 * 12/2010
JP     2009-158921 A   *  7/2009

(Continued)

OTHER PUBLICATIONS

Kitszawa, Daisuke et al, "Electron-donating organic materials for photosensors", XP-002672556, Database Ca [Online] Chemical Abstracts Service, Columbus, Ohio, Jul. 17, 2009, (2 pages).

(Continued)

*Primary Examiner* — Peter D Mulcahy
*Assistant Examiner* — Henry Hu

(57) ABSTRACT

High performance organic photovoltaic cells based on donor acceptor polymers in the active layer. A composition comprising: at least one copolymer comprising at least one first donor moiety and at least one first acceptor moiety in the copolymer backbone, wherein the first acceptor moiety comprises at least one first ring which is bivalently linked to the copolymer backbone and at least one second ring fused to the first ring and not bivalently linked to the copolymer backbone, wherein the first ring or the second ring comprises two adjacent fluoro ring substituents, and optionally, wherein the donor comprises at least one fused ring system. High efficiency, high Voc, and a combination of both can be achieved.

31 Claims, 1 Drawing Sheet

(51) Int. Cl.
*C07D 513/04* (2006.01)
*H01L 51/00* (2006.01)
*H01L 51/42* (2006.01)
*C09B 57/00* (2006.01)
*C09B 69/10* (2006.01)

(52) U.S. Cl.
CPC . *C08G 2261/3246* (2013.01); *C08G 2261/414* (2013.01); *C08G 2261/91* (2013.01); *Y02E 10/549* (2013.01)

(56) References Cited

U.S. PATENT DOCUMENTS

2011/0023964 A1* 2/2011 Kitazawa et al. ............. 136/263
2013/0092912 A1* 4/2013 You ................................ 257/40
2014/0163193 A1* 6/2014 Zhou ................... H01L 51/0036 528/210

FOREIGN PATENT DOCUMENTS

| JP | 2009158921 | 7/2009 | |
| WO | WO-2009/125647 A1 * | 10/2009 | |
| WO | WO 2009125647 A1 | 10/2009 | |
| WO | WO-2011/060526 A1 * | 5/2011 | |
| WO | WO 2011060526 A1 | 5/2011 | |
| WO | WO 2011156478 A2 | 12/2011 | |

OTHER PUBLICATIONS

Invitation to Pay Additional Fees for PCT/US2011/064907 mailed Apr. 26, 2012 (10 pages).

* cited by examiner

FLUORO MONOMERS, OLIGOMERS, AND POLYMERS FOR INKS AND ORGANIC ELECTRONIC DEVICES

RELATED APPLICATION

This application claims priority to U.S. provisional application 61/423,571 filed Dec. 15, 2010, which is hereby incorporated by reference in its entirety.

INTRODUCTION

A need exists to provide better electronic and photonic devices including better solar cells or photovoltaic devices. If some aspects of the devices are based on organic, solution processable materials, including organic polymers, cost reduction can be achieved.

In particular, a need exists to provide better active layers for organic photovoltaic devices. These active layers can comprise a combination of p-type material and n-type material. The p-type material can be a conjugated polymer. The polymer ideally should satisfy a variety of chemico-physical properties, such as solubility, processability, good film formation, proper absorption properties, proper HOMO/LUMO (molecular orbitals and energy levels), bandgap, charge carrier mobility, and other properties. However, achievement of combinations of properties can be difficult, and gaining one property may result in the sacrifice of another.

For a review of organic photovoltaic technology, see, for example, Sun and Saraciftci (Eds.), *Organic Photovoltaics, Mechanisms, Materials, and Devices*, CRC, 2005.

US Patent Publication 2010/0252112 to Watson describes polymers comprising phthalimide units and/or head-to-head (H-H) substituted biheteroaryl units. Watson's Example 26, describes a polymer P26 that comprises fluoro substituents. However, the publication does not describe how to make the fluorinated monomer used to prepare the polymer 26. Moreover, the product oligomer or polymer, P26, was not characterized, and molecular weight was not measured. It was not clear or suggested that the polymer shown in example 26 would have any particular benefit when used in a photovoltaic device.

SUMMARY

Embodiments provided herein include monomers, oligomers, and polymers, as well as ink formulations and devices. Methods of making and methods of using the compositions and devices are also described.

One embodiment provides a composition comprising: at least one copolymer comprising at least one first donor moiety and at least one first acceptor moiety in the copolymer backbone, wherein the first acceptor moiety comprises at least one first ring which is bivalently linked to the copolymer backbone and at least one second ring fused to the first ring and not bivalently linked to the copolymer backbone, wherein the first ring or the second ring comprises two adjacent fluoro ring substituents, and optionally, wherein the donor comprises at least one fused ring system. In one embodiment, the donor does comprise at least one fused ring system.

Another embodiment provides a composition comprising at least one polymer comprising at least one first donor moiety and at least one first acceptor moiety, wherein the first acceptor moiety comprises at least one moiety represented by (I):

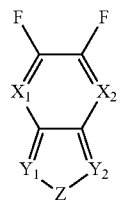

wherein X1 and X2 are, independently, carbon or nitrogen; Y1 and Y2 are, independently, nitrogen or carbon; and Z is a bridging moiety comprising at least one carbon atom or a heteroatom; and optionally, wherein the donor comprises at least one fused ring system. Moiety (I) can be linked to the copolymer chain via the X1 and X2 sites, or the Y1 and Y2 sites. The group Z can comprise a wide variety of moieties including, for example, one or more B, C, N, O, P, S, Se, and/or Si atoms, and combinations thereof.

Other embodiments include inks comprising these copolymers, coated substrates comprising these copolymers, and devices comprising these polymers. One particularly useful devices is a photovoltaic device.

Other embodiments relates to methods of making these copolymers including polymerization methods and methods of making the monomer. For example, another embodiment relates to a method comprising: providing a moiety represented by (I),

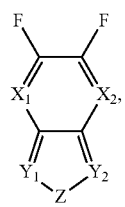

wherein X1 and X2 are, independently, carbon or nitrogen; Y1 and Y2 are, independently, nitrogen or carbon; and Z is a bridging moiety comprising at least one carbon atom or a heteroatom; and functionalizing the moiety (I) with at least two polymerization reaction sites.

Another embodiment provides a method comprising: providing a monomer precursor comprising at least one first ring fused with at least one second ring, wherein the first ring comprises at least two polymerization reaction sites, functionalizing the monomer precursor with at least two fluorine atoms on the first or second ring to form the monomer.

At least one advantage for at least one embodiment is high photovoltaic efficiency. At least one additional advantage for at least one embodiment is larger Voc. Another advantage for some embodiments is to have both high photovoltaic efficiency and high Voc, and/or the ability to find the best combination of Voc and efficiency for a particular application.

At least one additional advantage for at least one embodiment is ability to control band gap and HOMO and LUMO levels. Surprisingly, the HOMO can be shifted to more negative values. This can provide better air stability, for example.

At least one additional advantage for at least one embodiment is polymer solubility at ambient or room temperature (about 25° C.), including good solubility with higher molecular weight polymers. This allows for easier processing and film formation. Some polymers require heating for them to be soluble.

At least one additional advantage for at least one embodiments includes possible S-F interactions that can help to planarize the polymer backbone and/or improve charge mobility and chain packing.

At least one additional advantage for at least one embodiment includes possible advantageous phase segregation. Fluoro groups may surface migrate generating useful surface properties and vertical phase separation. This may be important in some embodiments such as an inverted solar cell.

At least one additional advantage for at least some embodiments is that a fluorine substitutent is able to have a powerful electronic effect with minimal impact on polymer chain conformation. Other electron withdrawing groups such as, for example, carbonyl or —$CF_3$ may impact conformation more.

Advantageous properties can be found for both outdoor and indoor photovoltaic applications.

DETAILED DESCRIPTION

Introduction

Figure 1:
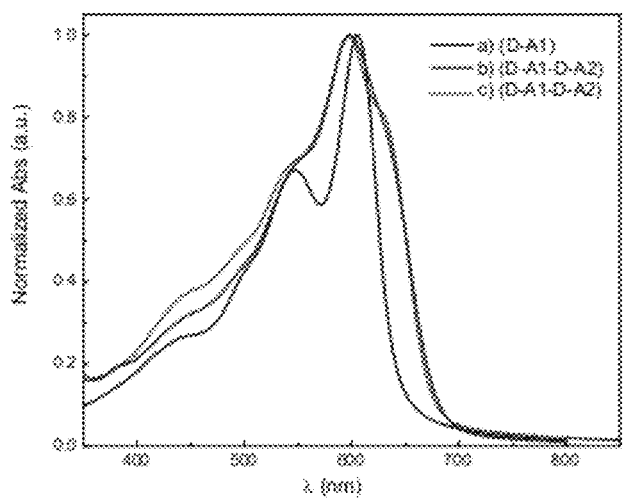
FIG. 1. Comparison of normalized UV-Vis absorption profiles of several solid-state benzobithiophene-based alternating Donor-Acceptor (D-A1) copolymers.

References cited herein are incorporated herein by reference in their entirety.

Prior patent filings related to donor-acceptor copolymers and organic electronic devices, including photovoltaic devices, assigned to Plextronics are incorporated herein by reference in their entirety including: U.S. patent Ser. No. 12/828,121 filed Jun. 30, 2010; Ser. No. 12/874,163 filed Sep. 1, 2010; and Ser. No. 12/874,137 filed Sep. 1, 2010. See also WO 2009/103030.

Part I

Polymer Description

Polymers and Copolymers

Polymers can comprise a backbone and side groups as known in the art. See, for example, Billmeyer, *Textbook of Polymer Science*, 1984. Copolymers are known in the art and comprise, for example, terpolymers and block copolymers, as well as alternating, non-alternating, and random copolymers. Copolymers can be prepared by polymerization of one or more monomers. Polymer blends can be prepared.

Conjugated polymers are described in, for example, T. A. Skotheim, *Handbook of Conducting Polymers*, 3rd Ed. (two vol), 2007; Meijer et al., *Materials Science and Engineering*, 32 (2001), 1-40; and Kim, *Pure Appl. Chem.*, 74, 11, 2031-2044, 2002.

Conjugated polymers can be used in photovoltaic active layers as a p-type material. The p-type active material can comprise a member of a family of similar polymers which have a common polymer backbone but are different in the derivatized side groups to tailor the properties of the polymer.

Conjugated polymers can comprise planarized backbone and increasing conjugation length before conjugation is interrupted.

Molecular weight of the polymer can be, for example, at least about 10,000, or at least about 20,000, or at least about 40,000, or about 10,000 to about 1,000,000, or about 25,000 to about 500,000, or about 25,000 to about 100,000, or about 25,000 to about 40,000'(number average molecular weight, Mn). Polydispersity can be, for example, about 1.5 to about 4.0, or about 1.5 to about 3.0, or about 2.0 to about 2.8.

The copolymer can be soluble or be highly dispersed in a solvent. For example, it can be dissolved or highly dispersed in a solvent like a polar aprotic or a polar protic solvent or a non-polar solvent. The solvent can be, for example, an organic solvent such as aromatic or non-aromatic, halogenated or non-halogenated hydrocarbons. Examples include chlorobenzene, chloroform, and toluene. The concentration of the polymer in the solvent can be at least 1 mg/mL, or at least 5 mg/mL, or at least 10 mg/mL. The solubility preferably is achieved at about room temperature, or about 25° C. If desired, heat can be applied to encourage solubility.

Conjugated polymers, including donor-acceptor conjugated polymers, may need solubilizing side groups for the polymer to be soluble, particularly at higher molecular weights, because the backbone is rigid. Flexible side groups can help to solubilize the polymer. The solubilizing group can be, for example, an optionally substituted alkyl or heteroalkyl, or optionally substituted aryl or heteroaryl group. The solubilizing group can comprise, for example 1-25, or 2-20 carbon atoms. Mixtures of solubilizing groups can be used. Solubilizing groups can be linear, branched, or cyclic. Mixtures of solubilizing groups can be used. In the present description, solubilizing groups as side groups are typically designated as R groups, e.g., R1, R2, R3, and the like. One skilled in the art can determine the type and amount of solubilizing groups which facilitate solubility. Hydrogen is not usually a solubilizing group.

Donor-Acceptor Copolymers

An important embodiment is the donor-acceptor polymer, which is known in the art. See, for example, Zhang et al., *J. Am. Chem. Soc.*, 1995, 117, 4437-4447; Sun and Saraciftci (Eds.), *Organic Photovoltaics, Mechanisms, Materials, and Devices*, CRC, 2005. See also, for example, U.S. patent Ser. No. 12/828,121 filed Jun. 30, 2010; Ser. No. 12/874,163 filed Sep. 1, 2010; and Ser. No. 12/874,137 filed Sep. 1, 2010. See also WO 2009/103030.

Donor-acceptor structures can be alternating or random as known in the art and as determined by the polymer synthesis. For example, an alternating structure can be represented as -(D-A)$_n$- (D-A regular alternating donor-acceptor repeating units) and a random structure can be -(D$_x$A$_y$)- (wherein D and A are randomly dispersed and x and y represent the relative amounts of the D and the A). Segmented copolymers can be made wherein donor and acceptor units are included in dimers, trimers, and oligomers, and these dimers, trimers, and oligomers are subjected to further polymerization.

The donor-acceptor structure can be tuned and adapted to provide lower band gaps and/or better absorption properties. See, for example, Hellström et al., *Dalton Trans.*, 2009, 10032-10039, 2009; Inganas et al., *Accounts Chemical Research*, 42, 11, 1731-1739, November 2009; Petersen et al., *Solar Energy Materials & Solar Cells*, 91, 2007, 996-1009.

A wide variety of donors are known. See, for example, a) Scharber, et al. *Adv. Mater.* 2006, 18, 789-794; b) van Mullekom, et al. *Materials Science and Engineering*, 32 (2001) 1-40.

A wide variety of acceptors are also known. See, for example, Leclerc et al. *J. Am. Chem. Soc.* 2008, 130, 732-742.

Acceptors

The copolymer can comprise at least one first acceptor moiety in the copolymer backbone. The first acceptor moiety can comprise at least one first ring which is bivalently linked to the copolymer backbone and at least one second ring fused to the first ring and not bivalently linked to the copolymer backbone. The acceptor moiety can comprise, for example, at least one benzothiadiazole moiety, or at least one quinoxaline moiety, or at least one thieno[3,4-b]pyrazine moiety.

The first ring or the second ring can comprise two adjacent fluoro ring substituents. If the acceptor comprises a quinoxaline moiety, the benzene ring of the quinoxaline can comprise the two adjacent fluoro ring substituents, or the pyrazine ring can comprise the two adjacent fluoro ring substituents.

The acceptor moiety can be represented by, for example, structure (I):

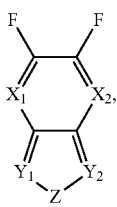
(I)

wherein X1 and X2 can be, independently, carbon or nitrogen; Y1 and Y2 can be, independently nitrogen or carbon. The group Z can comprise a wide variety of moieties including, for example, one or more B, C, N, O, P, S, Se, and/or Si atoms, and combinations thereof. In particular, Z can be S, N, or an optionally substituted carbon moiety such as a C1 or C2 moiety illustrated further in structures herein. The number of carbons in the Z moiety can be adapted allow for ring formation.

X1 and X2 can be the bivalent linkage sites to the copolymer backbone, particularly if X1 and X2 are carbon. Alternatively, Y1 and Y2 can be the bivalent linkage sites to the copolymer backbone, particularly if Y1 and Y2 are carbon.

Six examples of embodiments for structure (I) are provided in structures (II), (III), (IV), (V), (VI), and (VII):

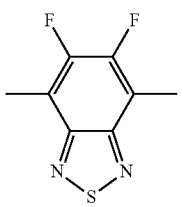
(II)

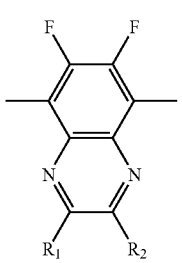
(III)

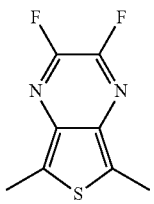
(IV)

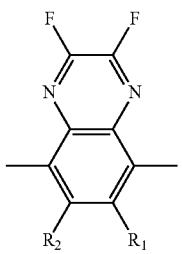
(V)

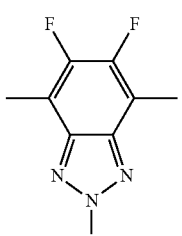
(VI)

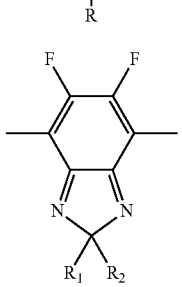
(VII)

The first ring can be an aromatic ring or a pseudoaromatic ring. The first ring can be a benzene ring or a heterocyclic ring. The first ring can be a five-membered ring or a six-membered ring. The heterocyclic ring can comprise, for example, sulfur. For example, in structures II, III, V, VI, and VII, the first ring is a benzene ring. In structure IV, the first ring is a heterocyclic ring comprising sulfur, e.g., thiophene.

The second ring can be a heterocyclic ring, and the heterocyclic ring can comprise nitrogen including two or three nitrogen atoms. The second ring can also comprise sulfur including a single sulfur atom. Examples of second rings include thiadiazole (structure II) or pyrazine (structure III, IV, or V) or triazole (structure VI).

Structures such as (II), without the fluoro groups, are known in the art: a) Heeger et al. *J. Am. Chem. Soc.*, 2007, 130, 3619; b) Inganas, O. et al. *J. Am. Chem. Soc.*, 2007, 131, 14612; c) Biniek, L. et al. *J. Mater. Chem.*, 2009, 19, 4946. Synthesis can be adapted to introduce fluoro units.

Structures such as (III), without the fluoro groups, are known in the art: a) Argiri Tsami et al. *J. Mater. Chem.*, 2007, 17, 1353; b) M. Leclerc et al. *J. Am. Chem. Soc.*, 2007, 130, 732. Synthesis can be adapted to introduce fluoro units. In another embodiment, the group III can be characterized by R1 and R2 are each hydrogen (see III-A).

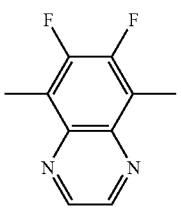
(III-A)

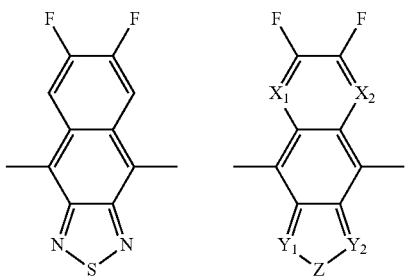

Structures such as (IV), without the fluoro groups, are known in the art and can be called a thieno[3,4-b]pyrazine. See, for example, Kenning et al., *J. Org. Chem.*, 2002, 67, 9073-9076; Wen et al., *Synthetic Metals*, 159 (2009) 2299-2301; Wen et al., *J. Org. Chem.*, 2008, 73, 8529-8536; Li, J.-C. et al. *Macromolecular Research*, 2010, 18, 304. Synthesis can be adapted to introduce fluoro units.

Structures such as (V), without the fluoro groups, are known in the art: e.g., Lee, J.-Y. et al. *J. Mater. Chem.*, 2009, 19, 4938, or Mastalerz, M. et al. *Organic Letters*, 2009, 11, 4500. Synthesis can be adapted to introduce fluoro units. In another embodiment, the group V can be characterized by R1 and R2 being hydrogen as shown in V-A:

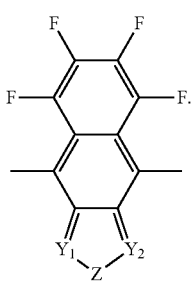

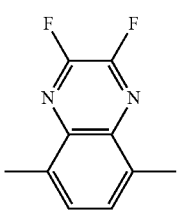
(V-A)

Methods known in the art can be used and adapted to prepare structures VI and VII. A particular example for VII is:

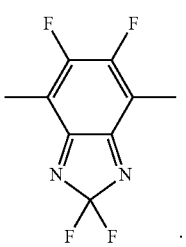

Examples of rings which have adjacent fluoro groups are known. See, for example, ortho positions on a benzene ring having two fluoro substituents ortho to each other. See, for example, 3,4-difluorobenzene. See, for example, Bashore et al., *Organic Letters*, 2006, 8, 26, 5947-5950.

Second Acceptor

The copolymer can comprise at least two different acceptor moieties which can be called a first and second acceptor moiety. A wide variety of acceptor moieties are known in the art in the context of donor-acceptor copolymers. See, for example, U.S. patent application Ser. No. 12/828,121 filed Jun. 30, 2010; Ser. No. 12/874,163 filed Sep. 1, 2010; and Ser. No. 12/874,137 filed Sep. 1, 2010, which are each incorporated by reference in their entirety including listings of acceptors. For example, the second acceptor moiety can comprise at least one moiety represented by (VIII):

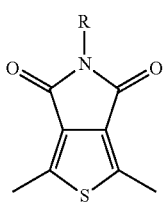
(VIII)

wherein R is not particularly limited but can be a solubilizing group. Examples of R include optionally substituted alkyl and heteroalkyl and optionally substituted aryl and heteroaryl. R can comprise, for example, 1-25, or 2-20 carbon atoms. R can comprise oxygen and can be fluorinated. R can be linear or branched alkyl.

Additional examples of the second acceptor include:

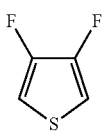
(IX-A)

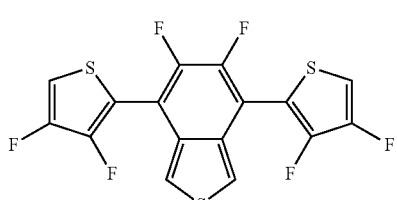
(IX-B)

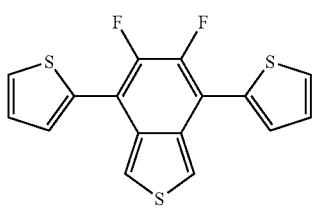
(IX-C)

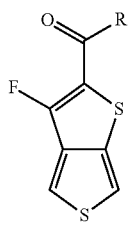
(IX-D)

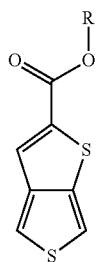
(IX-E)

R can be, for example, a solubilizing group, as described herein, or hydrogen.

For the last two acceptors on the right, IX-D and IX-E, see for example, Chen, H.-Y. et al. *Nature Photonics,* 2009, 3, 649. The acceptor structures shown in IX-A to IX-E above can be adapted to show polymerization reaction sites for monomer structures or bivalent linkage to the polymer chain after polymerization. For example, the structures IX-A to IX-E can be bonded to the polymer chain at the 2- and/or 5-positions of the thiophene ring.

As part of a larger molecule, including a polymer for example, the structure VIII can be part of another larger moiety such as, for example, XIA or XIB:

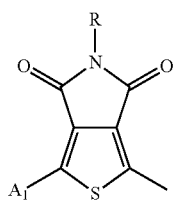
(XIA)

wherein A1 comprises a thiophene ring linked to (I) at the two or five position of the thiophene ring; and

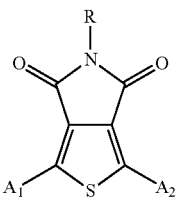
(XIB)

wherein both A1 and A2 comprise thiophene ring linked to (I) at the two or five position of the thiophene ring. The thiophene rings in XIA and XIB can be part of a fused ring structure.

In addition, polymers can be prepared wherein the polymer backbone comprises the moiety (XII):

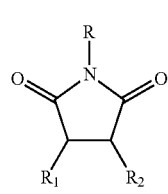
(XII-A)

wherein moiety XII is linked bivalently to the polymer backbone via the R1 and R2 groups, which can form a ring. In structure V, the carbon atoms 3 and 4 of the pyrrole ring can be joined by a double bond to form part of an extended conjugated polymer chain, as shown in structure XII-B:

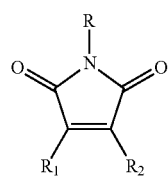
(XII-B)

The R1 and R2 groups can link together to form a ring, including for example a five- or six-membered ring including an all-carbon ring or a ring comprising a heteroatom, including a heterocyclic ring, including, for example, a thiophene ring or a benzene ring. The ring formed by R1 and R2 can be aromatic or pseudoaromatic. The ring can be bivalently functionalized so it can be incorporated into the polymer backbone.

Structure VIII is an embodiment of structures XI-A and XI-B. Another example is structure XI-C:

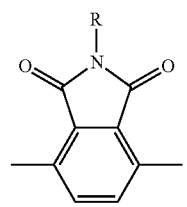
(XI-C)

Polymers can be also prepared which comprise at least one backbone moiety represented by:

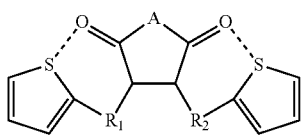

(XII)

wherein A can be an optionally substituted alkylene moiety (e.g., optionally substituted methylene or ethylene, —(CH$_2$)$_x$— or a heteroatom, and wherein the moiety XII is bivalently linked to the polymer backbone via the illustrated thiophene rings linked to the R1 and R2 groups. In XII, although a non-covalent interaction is illustrated as a dashed line between the thiophene ring sulfur and the carbonyl oxygen, such interaction is optional and not required. The thiophene rings can be linked to the polymer at their 2- and 5-positions. The thiophene rings can be linked to additional thiophene rings.

As with structure XI, in structure XII, the carbon atoms 3 and 4 of the top ring comprising alkylene or heteroatom A can be joined by a double bond to form part of an extended conjugated polymer chain, as shown in structure XII-B:

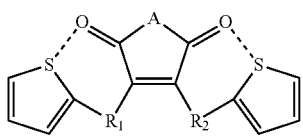

(XII-B)

In the heteroatom embodiment for A, A can be, for example, nitrogen, oxygen, sulfur, or selenium. The nitrogen, if the heteroatom A, can be functionalized as shown in I. The R group in structure I is adapted for bonding to a nitrogen atom. In other structures such as VI, described herein, R can bind to other atoms besides nitrogen, and R can be adapted accordingly.

In a manner similar to structure V, R$_1$ and R$_2$ can form five or six-membered rings, including aromatic or pseudoaromatic rings, including heterocyclic rings, including benzene ring or thiophene ring.

Aromatic rings structures including aromatic rings structures, including benzidine ring structures, and biphenyl structures, can be used.

In addition, polymers can be also prepared wherein the backbone comprises a structure represented by XIII-A:

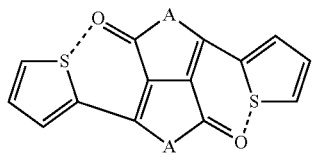

(XIII-A)

Here, A can be an optionally substituted alkylene or heteroatom such as, for example, N, O, S, or Se, as described above. The A group can comprise substituents such as the R group in structure VIII. For example, the R group in structure XIII-A can be adapted for bonding to a nitrogen atom. In structures such as XIII-A described herein, R can bind to other atoms besides nitrogen, and R can be adapted accordingly.

The structure XIII-A can be linked into the polymer chain via the illustrated thiophene rings.

As with other structures described herein, the R groups in structure XIII-A in one or more polymers can be varied, and different R groups can be used such as, for example, R1, R2, R3, or R', R", R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different. The R groups can be solubilizing group, helping to create or enhance solubility.

Additional Embodiments for the Acceptor

In additional embodiments, the first acceptor can have at least one third ring which is not bivalently linked to the polymer chain as shown below in structures X. Additional embodiments for the first acceptor include:

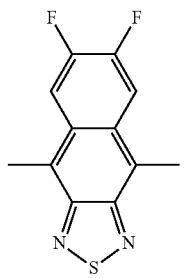

X-A

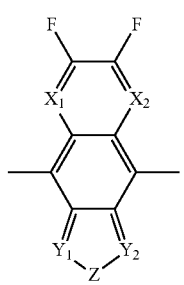

X-B

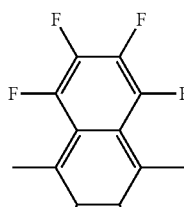

X-C

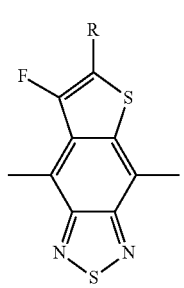

X-D

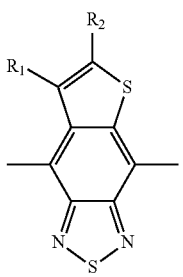
X-E

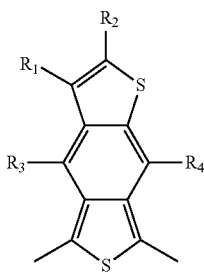
X-F

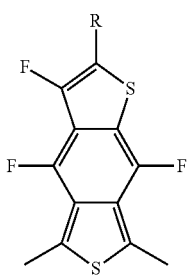
X-G

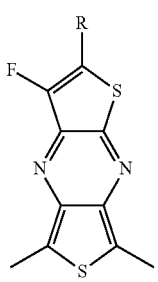
X-H

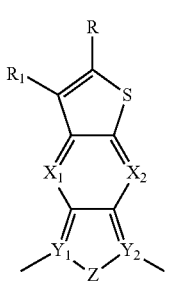
X-I

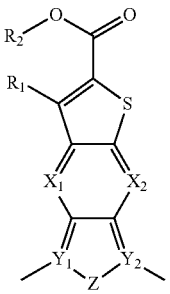
X-J

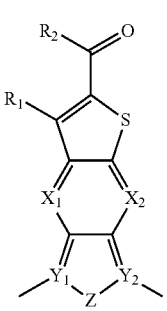
X-K wherein $Y_1$, $Y_2$, $Z$, $X_1$, and $X_2$ can be as described above. $R_1$, $R_2$, $R_3$, $R_4$ and R can be H or solubilizing groups including optionally substituted alkyl or aryl groups as well as halogen including a F atom.

The structures shown in X can be also adapted to not comprise two fluoro atoms and therefore also function as a second acceptor.

Donors

A wide variety of donor moieties are known in the art in the context of donor-acceptor copolymers. See, for example, U.S. patent application Ser. No. 12/828,121 filed Jun. 30, 2010; Ser. No. 12/874,163 filed Sep. 1, 2010; and Ser. No. 12/874,137 filed Sep. 1, 2010, which are each incorporated by reference in their entirety including listings of donors. Donors which are particularly electron rich can be used.

The donor moiety can comprise, for example, at least two, or at least three fused rings. The donor moiety can comprise, for example, at least one, or at least two thiophene rings. These can be fused to other rings.

The donor moiety can comprise at least three fused rings, wherein at least one, or both, of the rings at the outer ends of the moiety is a thiophene ring.

The donor moiety can be represented by three fused rings, -A-B-C-, wherein A and C are thiophene rings and B is a benzene ring or a pyrrole ring.

The donor moiety can be a benzodithiophene moiety including, for example, a benzo[1,2-b-4,5-b']dithiophene or a benzo[2,1-b-3,4-b']dithiophene. For example, one donor is shown below including showing how it can be functionalized with two polymerization reaction sites based on tin groups:

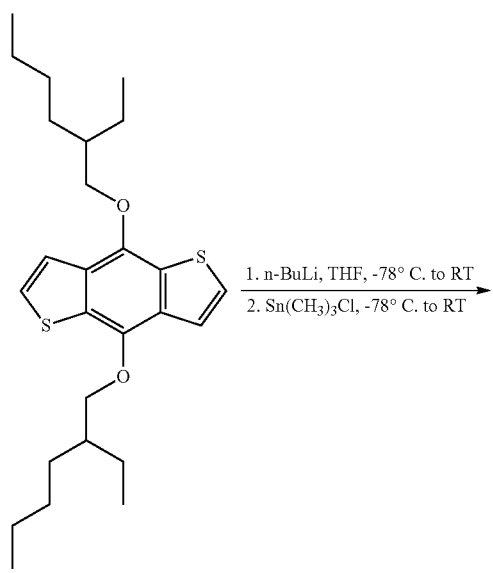

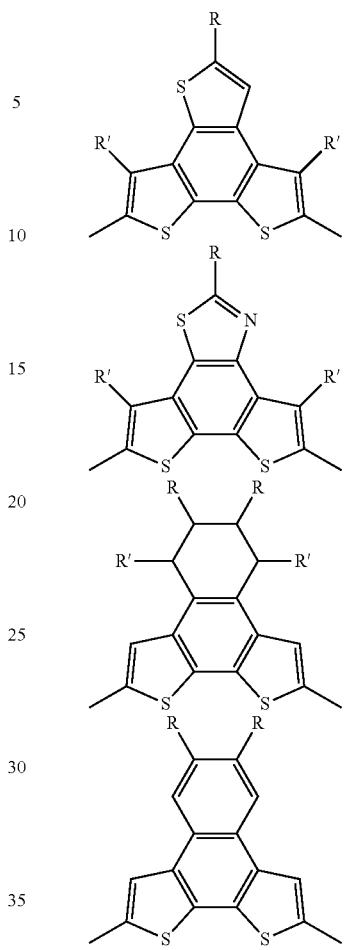

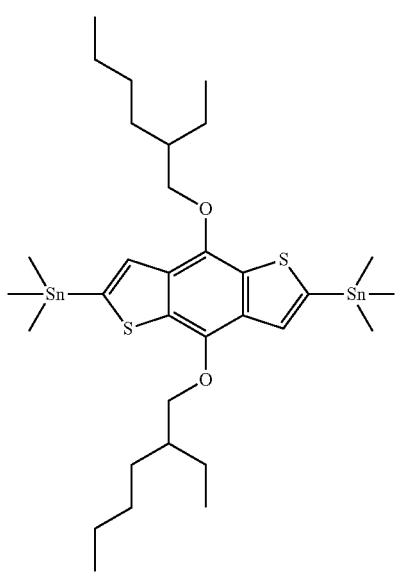

This monomer has relatively high symmetry. The alkoxy side group can be varied of course to be, for example, an optionally substituted alkyl group. Another example of a monomer with lower symmetry can be represented by:

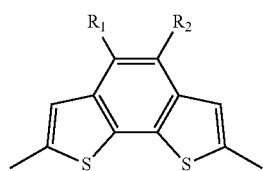

wherein R1 and R2 can comprise solubilizing groups. They can also form another ring, including an aromatic ring, as found in the following additional examples:

where R and R' are chosen independently in the same manner as for $R_1$ or $R_2$, generally.

Another example of a donor is the dithieno[3,2-b:2',3'-d] pyrrole (DTP) repeat unit, wherein the DTP repeat unit can be represented by:

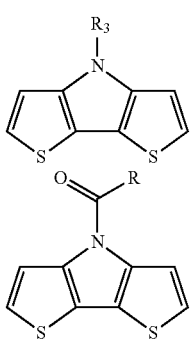

wherein R3 can be, for example, branched alkyl chain, fluorinated, or carbonyl. See, for example, Evenson, et al., *Org. Lett.*, 2010, 12, 4054. See also, for example, WO 2009/103030 to Sheina et al. (Plextronics). R can be a wide variety of groups including, for example, H and a solublizing group. These repeat units can be incorporated into the polymer chain at the 2- and 5-positions of the thiophenes.

The copolymer can comprise at least one second donor different from the first. Additional examples of donors include:

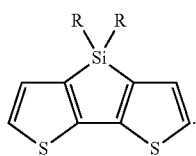

wherein R can be a branched or unbranched alkyl, for example.

Another embodiment for a donor comprises:

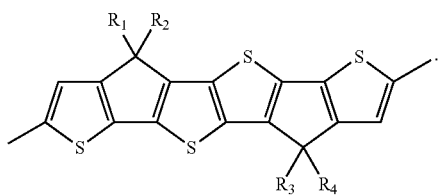

(I)

wherein R$_1$, R$_2$, R$_3$, and R$_4$ are independently hydrogen or solubilizing groups. See for example U.S. provisional application No. 61/407,419 filed Oct. 27, 2010. An example of a polymer is shown below, wherein the benzothiadiazole unit on the right can be fluorinated on the phenyl ring as described herein.

tions: *A Practical Guide*, Ed. Miyaura, 2002; (b) *Handbook of Organopalladium Chemistry for Organic Synthesis*, Ed. Negishi, 2002; (c) Kuwano, R, Utsunomiya, M., Hartwig, J. F., *J. Org. Chem.*, 2002, 67, 6479-6486; (d) Yu et al. *J. Am. Chem. Soc.* 2009, 131, 56; (e) Hou, J.; Park; M.-H.; Zhang, S.; Yao, Y.; Chen, L.-M.; Li, J.-H.; Yang, Y. *Macromolecules*, 2008, 41 (16), 6012-6018; (f) Blouin, N.; Michaud, A.; Gendron, D.; Wakim, S.; Blair, E.; Neagu-Plesu, R.; Belletête, M.; Durocher, G.; Tao, Y.; Leclerc, M. *J. Am. Chem. Soc.* 2008 130 (2), 732-742; (g) Swager et al. *Adv. Mater.* 2001, 13, 1775; (h) Koeckelberghs et al. *Macromolecules.* 2007, 40, 4173; (i) High-Efficient-Low-Cost Photdvoltaics, Springer Verlag Berlin Heidelberg, 2009, Editors: Petrova-Kock, V.; Goetzberger, A., 195-222.

Ratio of Donor and Acceptor and Microstructure

The ratio of donor to acceptor can be adapted for a particular application. Also, the ratio of different acceptors or different donors can be adapted for a particular application. The molar ratio of donor and acceptor can be one, less than one, or more than one. In other words, the polymer does not need to comprise equal molar amounts of donor and acceptor. The polymer can comprise more donor than acceptor, or more acceptor than donor. Chart I shows examples of this. For example, the ratio can be 2:1. The following list shows seven different embodiments for copolymer microstructure based on donors and acceptors:

-[D1-D2-A1]$_n$-
-[D1-D1-A1]$_n$-
-[(D1-A1)$_x$-(D2-A2)$_y$]$_n$-
-[D1-A1)$_x$-(D1-A2)$_y$]$_n$-
-[(D1-D1-A1)$_x$-(D1-D1-A2)$_y$]-
-[(D1-D2-A1)$_x$-(D1-D2-A2)$_y$]-

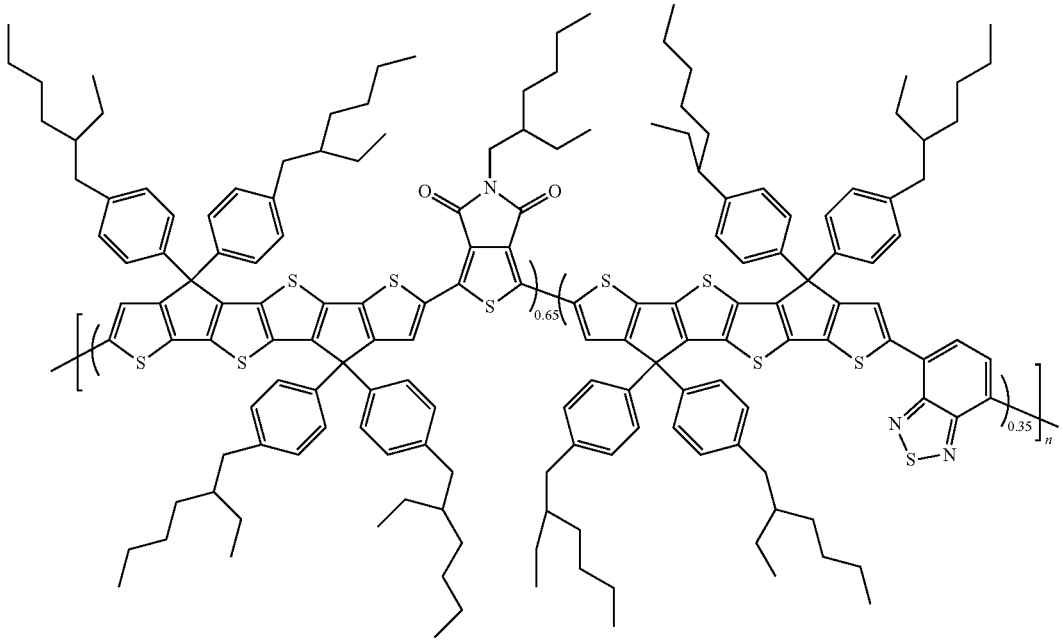

Polymerization

Known polymerization methods can be used to generate carbon-carbon bond formation including cross-coupling. For example, transition metal catalysts can be used in Suzuki coupling. For example, synthetic approaches include, for example, Yamamoto, Suzuki, Negishi or Stille couplings for polymerization. See, for example (a) *Cross-Coupling Reac-*

Different copolymer microstructures can be prepared as known to those skilled in the polymer chemistry arts. For example, random copolymer structures can be produced. Mixed monomer polymerization can be carried out. Non-random copolymer structures can be produced. Alternating structures can be made. Monomers can be converted to segments are oligomers, and then the segments or oligomers polymerized.

Additional Embodiments Including High Performance Embodiments

Some embodiments provide particularly high performance in, for example, photovoltaic and/or solar cell testing including excellent power conversion efficiency and open circuit voltage. See, for example, working examples below and devices prepared therefrom and polymers used in the devices. The embodiments comprise, for example, monomers, oligomers, polymers, inks, devices, and methods of making and using same.

For example, one embodiment provides a device comprising: at least one cathode; at least one anode; at least one photovoltaic active layer disposed between the cathode and anode and comprising at least one p-type material and at least one n-type material, wherein the p-type material comprises at least one polymer comprising a donor-acceptor structure, comprising a second acceptor backbone moiety:

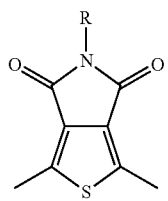

(VIII)

wherein R comprises a solubilizing group; and wherein the donor comprises at least one benzodithiophene structure, and the polymer comprises at least one first acceptor other than (VIII) which is a fluorinated acceptor, such as structures I, II, III, IV, V, VI, or VII, and in particular structure II. Alternatively, the device can comprise a polymer comprising at least one first acceptor other than (VIII) which comprises a fluorinated benzothiadiazole structure and optionally comprises the benzodithiophene structure. In one embodiment, the first acceptor other than (VIII) comprises a fluorinated benzothiadiazole structure. In one embodiment, for example, the first acceptor other than (VIII) comprises a fluorinated benzothiadiazole structure, and the molar amount of the second acceptor is greater than the molar amount of the first acceptor. In one embodiment, the first acceptor other than (VIII) comprises a fluorinated benzothiadiazole structure, and (1) the molar amount of the second acceptor is 5% to 95%, and the molar amount of the first acceptor is 95% to 5%, relative to the total molar amount of the combined first and second acceptor structure, or (2) the molar amount of the second acceptor is 55% to 75%, and the molar amount of the first acceptor is 25% to 45%, relative to the total molar amount of the combined first and second acceptor structure. In one embodiment, the first acceptor other than (VIII) comprises a fluorinated benzothiadiazole structure, and the molar amount of the second acceptor is about 65%, and the molar amount of the first acceptor is about 35%, relative to the total molar amount of the combined first and second acceptor structure. In one embodiment, the benzodithiophene structure comprises at least one alkyl substituent. In one embodiment, the benzodithiophene structure comprises at least one C6-C12 branched alkyl or alkoxy structure. In one embodiment, the R group is a C6-C12 branched alkyl or alkoxy structure. In one embodiment, the polymer is a random polymer. In one embodiment, the polymer has a number average molecular weight of at least 10,000, or at least 20,000. In one embodiment, the polymer is soluble in chloroform. In one embodiment, the device has a power conversion efficiency of at least 6%, or at least 7%, or at least 8%. In one embodiment, the device has an open circuit voltage of at least 0.9 V, or at least 1.0 V. In one embodiment, the device has a power conversion efficiency of at least 6%, and an open circuit voltage of at least 0.6 V, or at least 0.7 V, or at least 0.8 V, or at least 0.9 V, or at least 1.0 V. In one embodiment, the device has at least one hole transport layer disposed next to the active layer. In one embodiment, the device has at least one hole transport layer disposed next to the active layer, wherein the hole transport layer comprises at least one sulfonated regioregular polythiophene. In one embodiment, the device has at least one interfacial modification layer comprising at least one organic semiconductor doped with at least one metal. In one embodiment, the active layer is annealed. In one embodiment, the active layer is thermally annealed. In one embodiment, the active layer is solvent annealed. In one embodiment, the weight ratio of p-material and n-material is about 1:1.5 to about 1:4, or about 1:1.5 to about 1:3, or about 1:1.8 to about 1:2.2. In one embodiment, the active layer has a thickness of about 60 nm to about 250 nm, or about 60 nm to about 200 nm, or about 75 nm to about 80 nm. In one embodiment, the active layer is formed by deposition of an ink comprising at least one fluorinated solvent. Solvent blends and additives can be used.

One can adapt the ratio of monomer content to provide the best balance of higher molecular weight, solubility, film formation, and/or performance.

One can adapt the side groups of the monomer, such, as branching for example, to provide solubility, and/or electronic influence, and/or morphological assembly and control, on the polymer backbone as needed.

High performance polymers can be prepared by reaction of at least three monomers including (i) benzodithiophene monomer comprising at least two tin groups (or more generally, groups which will react with halogen in a polymerization reaction, (ii) a monomer comprising the structure (VIII) comprising at least two halogeno (e.g., two bromo) groups, and (iii) a fluorinated benzothiadiazole monomer comprising at least two halogeno (e.g., two bromo) groups. The side groups and ratio of monomers can be adapted to achieve best photovoltaic performance, solubility, and film formation. The ratio of donor and acceptor can be about 1:1. Polymerization conditions can be adapted to provide sufficient molecular weight. Polymerization can be carried out to produce random structures.

In one embodiment, structure VIII can be found in an oligomer including a dimer or trimer having multiple units of VIII linked together (see for example U.S. Ser. No. 12/874, 163). An example would be:

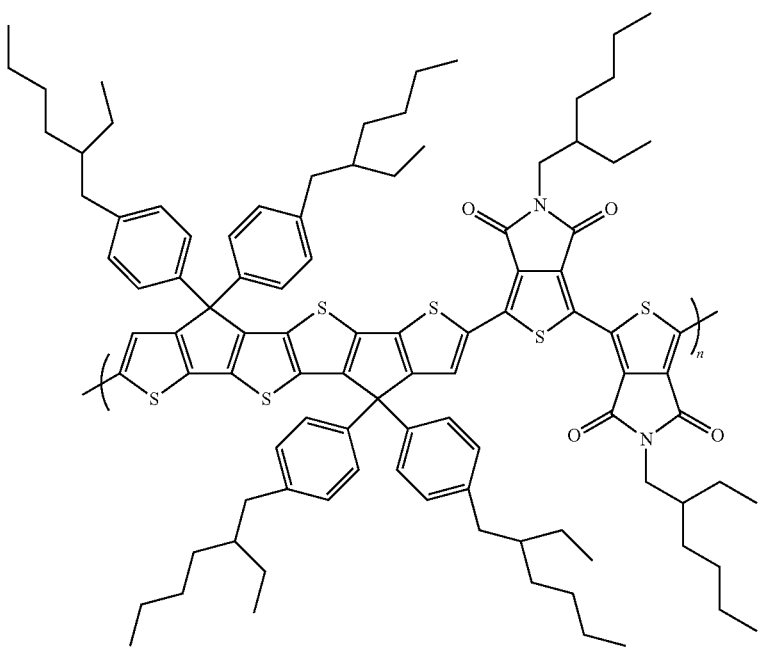

wherein the polymer is adapted to also include monomers such as (I), (II) and other monomers described herein including (III)-(VII).

After polymerization, the polymers providing high performance can be formulated with at least one solvent and at least one n-type material to provide an ink.

The first acceptor other than (VIII) can be a structure comprising at least two fused ring structures, or at least three fused ring structures. Benzothiadiazole (BTD) is an example of two fused ring structures. The benzo group of BTD can be fluorinated with one or two fluoro groups.

Polymers can be prepared which comprise three backbone moieties: a donor, and first and second acceptor moieties. Polymers can be prepared, in one embodiment, which comprise only the three backbone repeat units in Example 3. All other types of repeat units can be excluded in one embodiment.

Examples of high performance polymers include:

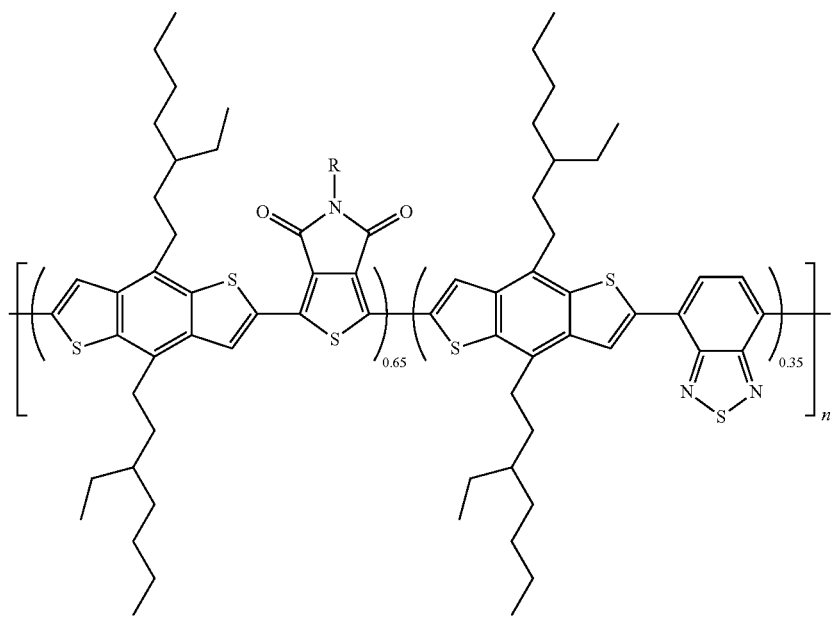

-continued

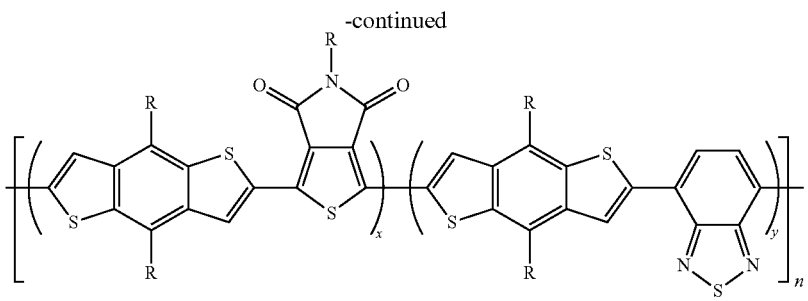

wherein R groups can be adapted to provide branching, solubility, and electronic tuning as described herein; values for x and y and n can be adapted for a particular application, and the BTD moieties can be fluorinated on the benzene ring with one or two fluoro groups, preferably two fluorogroups (not shown).

For example, additional structures include:

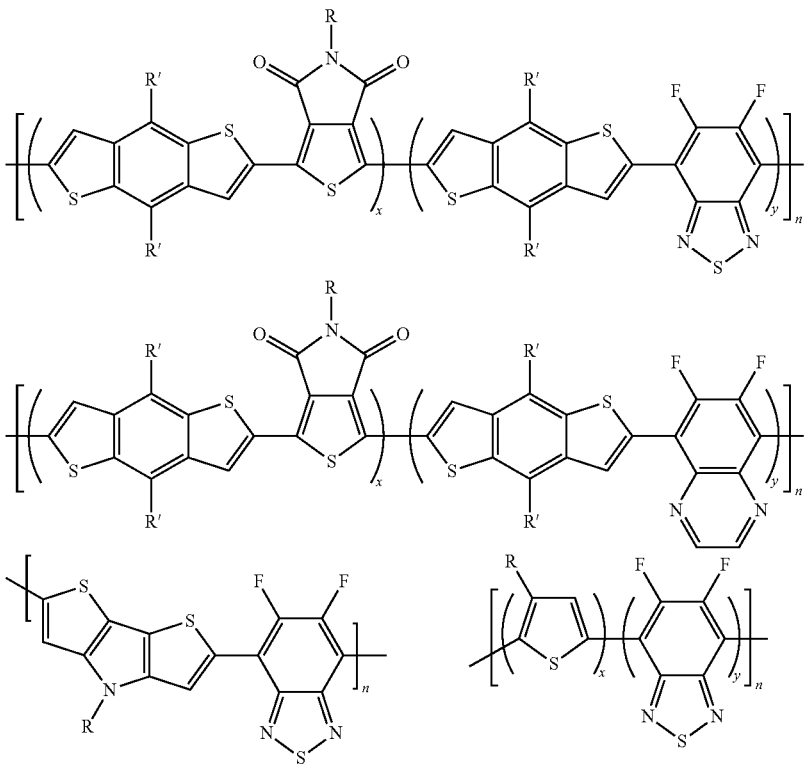

Exclusionary Embodiments

In one embodiment, the monomer structures in Watson 2010/0252112 can be excluded including the phthalimide units in paragraph 55 and the head-to-head (H—H) substituted biheteroaryl units in paragraph 115. These can be excluded so that the monomer content is less than 10 mole percent, less than one mole percent, less than 0.1 mole percent, or totally excluded (zero percent).

S-F or S-II Interactions

In one embodiment, the fluoro groups are able to encourage an intramolecular interaction with aromatic groups comprising fluoro and adjacent groups like S to help increase chain rigidity (e.g., "F-S interactions"). This increased rigidity can result in better electron delocalization and charge carrier mobility leading to better device performances. Better photophyscial properties can be observed. The S-F interactions can be evaluated with, for example, 2D NMR.

See, for example, descriptions of the influence of fluoro in Yan et al., *Bull. Korean Chem. Soc.*, 2007, 28, 6, 959-964

Homo/Lumo Energy Levels

Embodiments can be prepared which provide for better absorption including more red absorption (e.g., about 700 nm to about 900 nm). HOMO/LUMO levels can be used to provide for better absorption, and include both theoretical calculations (e.g., Gaussian calculations, as provided below) and experimental measurements (e.g., cyclic voltametry).

Embodiments can be prepared which lower LUMO of the acceptor (e.g., less than −3.6 eV).

Embodiments can be prepared which can be used with electron rich donor-building blocks to decrease HOMO (e.g., shift lower by about 0.4 eV). This can provide for a higher Voc and increased OPV efficiency. HOMO and LUMO calculations are described further hereinbelow.

One can match the acceptor(s) and donor(s) in view of their HOMO and LUMO levels.

Part II

Monomer Synthesis

For monomer structures comprising moieties such as, for example, (I), (II), (III), (IV), (V), (VI), and (VII), the synthesis can comprise two alternative pathways: (1) put the polymerization groups on the ring structure first followed by later putting fluoro groups on the ring structure, or (2) put the polymerization groups on the ring structure only after first putting fluoro groups on the ring structure. Herein, pathway number (2), in particular, has been found to provide one or more advantages.

In general, one can provide at least one monomer precursor. The precursor can be functionalized with at least two polymerizable groups (step A). The precursor can be also functionalized with at least two fluoro groups (step B). The fluoro groups can be adjacent to each other. In one embodiment, step A is carried out before step B. In another embodiment, step B is carried out before step A.

For example, one embodiment provides a method comprising: providing a moiety represented by (I),

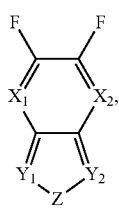

(I)

wherein X1 and X2 are, independently, carbon or nitrogen; Y1 and Y2 are, independently, nitrogen or carbon; and Z is a bridging moiety comprising at least one carbon atom or a heteroatom; and functionalizing the moiety (I) with at least two polymerization reaction sites.

The yield of the reaction providing the two polymerization reaction sites can be, for example, at least 10%, or at least 20%, or at least 30%.

The polymerization reaction sites can be adapted to be nucleophilic or electrophilic. The polymerization can result in carbon-carbon bond formation. Transition metal catalysis (or initiation) can be used.

In one embodiment, the functionalizing with polymerization reaction sites occurs at X1 and X2. In one embodiment, functionalizing with reaction sites occurs at Y1 and Y2.

In one embodiment, the polymerization reaction sites are halogen including bromine.

In some embodiments, the structure (I) is represented by one of:

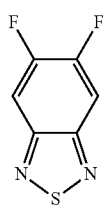

(II)

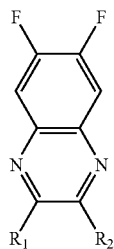

(III)

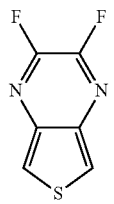

(IV)

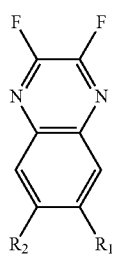

(V)

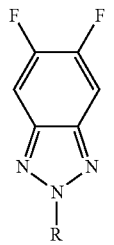

(VI)

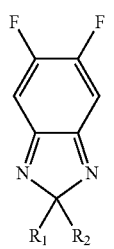

(VII)

In one embodiment, the providing step comprises providing a first fluorinated compound comprising a first ring, followed by carrying out a ring closure reaction to generate a second ring fused to the first ring. In one embodiment, the providing step comprises providing a first fluorinated compound comprising a first ring functionalized with at least two amino groups, followed by carrying out a ring closure reaction with the amino groups to generate a second ring fused to the first ring. In another embodiment, the providing step comprises providing a first fluorinated compound comprising a first ring functionalized with at least two primary amino groups in an ortho position on the ring, followed by carrying out a ring closure reaction with the primary amino groups to generate a second ring fused to the first ring.

The ring closure reaction can be carried out with a yield of, for example, at least 25%, or at least 35%, or at least 45%, or at least 53%, or at least 60%.

Compounds providing a core ring structure and at least two fluoro atoms, including two adjacent fluoro atoms, are available and known in the art. One example is 4,5-difluorobenzene which can be functionalized further with, for example, amino groups (e.g., 4,5-difluorobenzene-1,2-diamine).

For structure II, an example of the synthetic methods is shown in the working examples.

Another embodiment provides a method comprising: providing a monomer precursor comprising at least one first ring fused with at least one second ring, wherein the first ring comprises at least two polymerization reaction sites, functionalizing the monomer precursor with at least two fluorine atoms on the first or second ring to form the monomer.

In one embodiment, the polymerization reaction sites are halogeno sites. In one embodiment, the polymerization reaction sites are bromine sites.

In one embodiment, the functionalizing is carried out on the first ring. In one embodiment, the functionalizing is carried out on the second ring.

In one embodiment, the first ring is a benzene ring or a thiophene ring. In one embodiment, the second ring is a heterocyclic ring.

In one embodiment, the monomer is represented by (polymerization reaction sites represented by "dangling bonds," particular atoms like a halogen like bromine not shown):

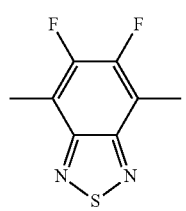

(II)

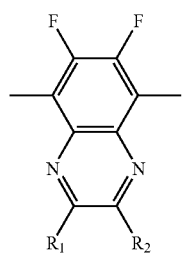

(III)

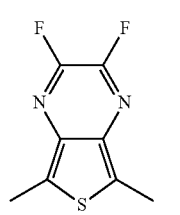

(IV)

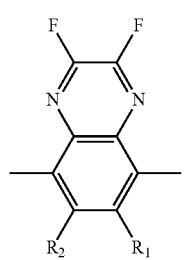

(V)

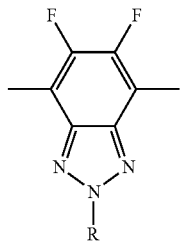

(VI)

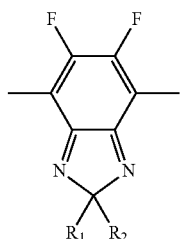

(VII)

wherein R1 and R2 and R are hydrogen or a solubilizing group.

In one embodiment, the monomer is represented by (dangling bonds are polymerization reaction sites):

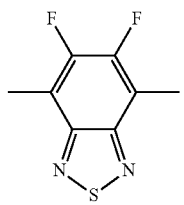

Part III

Uses Including Ink Formulation and Devices

Uses of Polymers

The materials, monomers, dimers, trimers, oligomers, polymers, and copolymers described herein in Part I, the working examples, and claims, can be used in organic electronic devices including, for example, OLEDs, OPVs including as OPV active layer, transistors, OFETs, batteries, and printed electronics generally, as well as sensors. The methods described in Part II can be adapted for the particular compounds and polymers being used.

For example, photovoltaic cells (solar cells) are known in the art. See, for, example, Sun and Sariciftci, *Organic Photovoltaics, Mechanisms, Materials, and Devices,* 2005. The photovoltaic cell can comprise an active layer comprising a composition comprising at least one p-type material and at least one n-type material. One can engineer HOMO, LUMO, and band gaps for the p- and n-type materials for good performance. The morphology of the active layer can be adapted to provide good performance. For example, a nanoscale morphology can be prepared. An example is a bulk heterojunction. Bilayers can be made as described in, for example, Ayzner et al., *J. Phys. Chem. C.,* 2009, 113, 20050-20060 (e.g., describing all solution-processed bilayers in solar cells).

The photovoltaic device can comprise at least one cathode, at least one anode, and at least one photovoltaic active layer disposed between the cathode and anode. The active layer can comprise a p-type material and an n-type material.

In an OPV active layer, the polymers described herein, which can be a p-type material, can be combined with n-type materials or acceptor moieties, such as, for example, fullerenes and fullerene derivatives. An example of a fullerene derivative is PCBM. Fullerenes can be also derivatized, as described in, for example, PCT Patent Publication WO 2008/018931 filed May 2, 2007 and US Patent Publication 2008/0319207 published Dec. 25, 2008, both to Laird, et al. (Plextronics, Inc.). Other types of n-type materials known in the art can be used. If desired, larger area photovoltaics can be fabricated. See, for example, Bundgaard et al., *Solar Energy Materials and Solar Cells,* 2007, 91, 1019-1025.

Polymer solar cells, including polymer fullerene solar cells, are described in, for example, Hoppe et al., *Adv. Polym. Sci.* (2008), 214: 1-86; Zhu et al., "Design Rules for Efficient Organic Solar Cells," Chapter 13, 195-222 in *High-Efficient Low-Cost Photovoltaics*, Springer, 2009.

OLED devices are known in the art including white OLEDs, or WOLEDs. See, for example, Li and Meng, *Organic Light Emitting Materials and Devices*, CRC Taylor, 2006 and US Patent Publication 2006/0078761 published Apr. 13, 2006. The devices can comprise, for example, multi-layer structures including, for example, an anode, including a transparent conductor, such as a transparent conductive oxide (TCO) on glass or PET or PEN; a hole injection layer; an electroluminescent layer, such as a polymer layer; a conditioning layer, such as LiF, and a cathode, such as, for example, Ca, Al, or Ba.

Methods known in the art can be used to fabricate organic electronic devices including for example OLED devices. Methods known in the art can be used to measure brightness, efficiency, and lifetimes. OLED patents include for example U.S. Pat. Nos. 4,356,429 and 4,539,507 (Kodak). Conducting polymers which emit light are described in for example U.S. Pat. Nos. 5,247,190 and 5,401,827 (Cambridge Display Technologies). See also Kraft et al., "Electroluminescent Conjugated Polymers—Seeing Polymers in a New Light," *Angew. Chem. Int. Ed.,* 1998, 37, 402-428, including device architecture, physical principles, solution processing, multi-layer applications, blends, and materials synthesis and formulation, which is hereby incorporated by reference in its entirety.

In addition, printed electronics are generally known in the art. See, for example, *Printed Organic and Molecular Electronics*, Ed. D. Gamota et al., 2004. For example, Chapters 1 and 2 describe organic semiconductors, Chapter 3 describes manufacturing platforms for printing circuits, Chapter 4 describes electrical behavior of transistors and circuits, Chapter 5 describes applications, and Chapter 6 describes molecular electronics. See also Pope et al., *Electronic Processes in Organic Crystals and Polymers,* 1999.

Solutions and Ink Formulations

The materials, polymers, and copolymers can be put into solution or dispersion form, including ink formulations, for further processing, adapting to the particular application at hand including electronic devices and organic electronic devices, such as, for example, OLED, solar cells and active layers of solar cells.

Lower cost electronic devices can be enabled because polymers, such as those described herein, can be processed into inks which can then be handled in the same manner as inks in conventional printing processes. Ink compositions used for forming, for example, the active layer of an organic photovoltaic device can be made by dissolving p-type and n-type materials in a solvent system, optionally containing other additives.

The solvents and conjugated polymer inks can be formulated or adapted for use in a particular application, such as a solar cell that may include additional additives, such as electron acceptors. The additive(s) and solvents can be adapted to provide good dispersability of the n- and p-type materials, solubility of the n- and p-type materials, and stability of the ink formulation. For example, solvents can be used which provide good solubility or dispersability for fullerenes or fullerene derivative n-type compounds. Solvents can be adapted to be environmentally friendly in view of regulations, and can be, for example, halogen free. In other embodiments additives can be included in the ink that can improve the final film morphology or other properties. For example, solvent additives disclosed in US Patent Publication entitled "Processing Additives for Fabricating Organic Photovoltaic Cells" 2009/0108255 to Bazan et al., published on Apr. 30, 2009 can be included.

Solvent(s) and solvent additive(s) can be removed from the ink compositions, and films can be formed. Solid films can be formed that either comprise solvent(s) and solvent additive(s), are substantially free of solvent(s) and solvent additive(s), or are free of solvent(s) and solvent additive(s). For example, the amount of remaining solvent can be less than about 5% by weight, or less than about 1% by weight, or less than about 0.1% by weight. For example, the amount of remaining solvent additive can be less than about 5% by weight, or less than about 1% by weight, or less than about 0.1% by weight.

Conventional methods can be used to cast polymer materials from the compositions to provide solid forms, including thin film forms and printed forms. For example, the p-type and n-type polymers of the active layer can be dissolved in the solvent to form an ink, and then allowed to dry. Suitable coating methods are known. These include roll-to-roll coating, screen printing, spin casting, spin coating, doctor blading, dip coating, spray coating, or ink jet printing, and other known coating and printing methods.

Exemplary embodiments include solvent systems based on a mixture of orthodichlorbenzene and trichlorobenzene.

Ink Components

Ink components known in the art can be used including, for example, solvents and n-type materials. The amounts of the components can be adapted to improve performance.

N-Type Materials

The active layer composition in, for example, a solar cell may include an n-type component or electron acceptor, or an electron acceptor moiety. These can be materials with a strong electron affinity and good electron accepting character. The n-type component should provide fast transfer, good stability, and good processability. The n-type material is desirably soluble in, dispersible in, or otherwise miscible with the solvents in order to provide for solution processing. The n-type component may take the form of particles, including microparticles and nanoparticles, inorganic particles, organic particles, and/or semiconductor particles.

For example, the active layer can comprise an n-type material comprising at least one fullerene structure. Fullerenes are known in the art. Fullerenes can be described as spheroidal carbon compounds. For example, the fullerene surface can present [6,6] bonding and [6,5] bonding as known in the art. The fullerene can have a surface comprising six-membered and five-membered rings. Fullerenes can be, for example, C60, C70, or C84, and additional carbon atoms can be added via derivative groups. See for example Hirsch, A.; Brettreich, M., *Fullerenes: Chemistry and Reactions*, Wiley-VCH Verlag, Weinheim, 2005, which is hereby incorporated by reference including teachings for fullerene nomenclature and synthesis, derivatization, reduction reactions (Chapter 2), nucleophilic additions (Chapter 3), cycloadditions (Chapter 4), hydrogenation (Chapter 5), radical additions (Chapter 6), transition metal complex formation (Chapter 7), oxidation and reactions with electrophiles (Chapter 8), halogenation (Chapter 9), regiochemistry (Chapter 10), cluster modification (Chapter 11), heterofullerenes (Chapter 12), and higher fullerenes (Chapter 13). Methods described herein can be used to synthesize fullerene derivatives and adducts.

In particular, the active layer can comprise at least one n-type material, wherein the n-type material comprises at least one derivatized fullerene or fullerene derivative. The derivative compound can be, for example, an adduct. The terms "derivatized fullerene," "fullerene derivative" as used herein, can be used interchangeably and can be, for example, fullerenes comprising, from 1 to 84, or 1 to 70, or 1 to 60, from 1 to 20, from 1 to 18, from one to ten, or from one to six, or from one to five, or from one to three substituents each covalently bonded to, for example, one or two carbons in the spheroidal carbon compounds. The derivatized fullerene can comprise a fullerene covalently bonded by [4+2] cycloaddition to at least one derivative moiety, R.

An example of an n-type material is PCBM.

Examples of n-type materials are described in, for example, International Patent Publication No. WO/2008/018931 published on Feb. 14, 2008 and US Patent Publication 2008/0319207 published Dec. 25, 2008, both to Laird, et al.

Solvent

The solvents can be polar or non-polar, or halogenated or non-halogenated. The solvents useful for the presently claimed inventions can include, for example, halogenated benzenes, alkyl benzenes, halogenated methane, and thiophenes derivatives, and the like. More specifically, solvent can be for example chlorobenzene, dichlorobenzene, trichlorobenzene, xylenes, toluene, chloroform, 3-methylthiophene, 3-propylthiphene, 3-hexylthiophene, butanone, fluorinated counterparts, and mixtures thereof. At least two solvents can be used.

The solvent system can include at least two solvents, at least one first solvent and at least one second solvent (e.g., a solvent additive), which are different from each other. They can be organic solvents. Particularly useful solvent systems can be used as described in co-pending US patent application entitled "Solvent System for Conjugated Polymers," published as 2008/0299293, to Sheina et al., and co-pending US patent application entitled "Improved Solvent System," Ser. No. 12/541,500 filed Aug. 14, 2009, which are hereby incorporated by reference in their entirety.

Solvent Additives

Solvent additives can be used, wherein a relatively small addition of a component (e.g., 1-6 wt % or 1-3 wt %) can have a large impact on performance. For example, a primary or first solvent can be used in conjunction with a solvent additive. Solvent additives can be volatile and can be removed upon solvent removal. Or solvent additives can be less volatile and stay in the film upon solvent removal:

Different examples exist for solvent additives. For example, a solvent additive can comprise at least one heterocyclic ring. The heterocyclic ring can be, for example, at least one thiophene ring. The second solvent can be for example an alkylthiophene. In some instances the heterocyclic ring is not a nitrogen-containing ring. Or it can be a nitrogen containing ring. Thus, in some embodiments the second solvent is or is not a pyridine, pyrazine, pyrimidine, or a pyrrolidinone. In some embodiments, the heterocyclic ring includes at least one S atom and at least one O atom. Examples of suitable solvent additives include, but are not limited to, thiophene derivatives (i.e., substituted thiophenes). The thiophene ring may be substituted or unsubstituted in different positions on the ring. However, in some instances the thiophene derivatives do not contain halogen atoms. Alkylthiophenes and combinations thereof may be used as the second solvent. The alkyl group can be, for example, C1, C2, C3, C4, and the like up to and including C8, C12, C16, and C20. The alkyl group can be linear or branched. Specific examples of suitable alkylthiophenes include methylthiophene, ethylthiophene, propylthiophene, butylthiophene, pentylthiophene, hexylthiophene, heptylthiophene, octylthiophene, nonylthiophene, and decylthiophene. Fluorinated solvents and additives can be used.

Other examples of solvent systems can be used as described in the aforementioned co-pending US patent applications, in US Patent Publication entitled "Processing Additives for Fabricating Organic Photovoltaic Cells"2009/0108255 to Bazan et al., published on Apr. 30, 2009 or in Peet, et al., "Efficiency enhancement in low-bandgap polymer solar cells, by processing with alkane dithiols," *Nat. Mater.*, 2007, 6, 497-500.

Device Preparation

Devices can be made comprising one or more layers comprising the polymers described herein and one or more electrodes, including anode and cathode. Layers can be built up on a substrate. See, for example, Chen et al., *Advanced Materials*, 2009, 21, 1-16.

Devices using the presently claimed inventions can be made using for example ITO as an anode material on a substrate. Other anode materials can include, for example, metals, such as Au, carbon nanotubes, single or multiwalled, and other transparent conducting oxides. The resistivity of the anode can be maintained below, for example, 15 Ω/sq or less, 25 or less, 50 or less, or 100 or less, or 200 or less, or 250 or less. The substrate can be rigid or flexible and can be, for example, glass, plastics (PTFE, polysiloxanes, thermoplastics, PET, PEN and the like), metals (Al, Au, Ag), metal foils, metal oxides, (TiOx, ZnOx) and semiconductors, such as Si. The ITO on the substrate can be cleaned using techniques known in the art prior to device layer deposition.

A variety of layers can be included between the anode and the active layer of a solar cell or the emissive layer of an OLED. These layers are generally referred to as hole transport layer (HTL), hole injection layers (HIL), hole collection (HCL), electron blocking layers (EBL) and/or interlayers.

Various kinds of hole transport layers, hole injection layers, hole collection layers, and/or hole extraction layers can be used. For example, hole transport layers of various kinds are described in the following references: 1) U.S. Pat. No. 7,569,159, issued Aug. 4, 2009 to Hammond et al.; U.S. Ser. No. 11/826,394, filed Jul. 13, 2007, published Oct. 9, 2008 as 2008/0248313; U.S. Ser. No. 12/422,159, filed Apr. 9, 2009; U.S. Ser. No. 61/108,851, filed Oct. 27, 2008; and U.S. Ser. No. 61/115,877, filed Nov. 18, 2008.

Hole transport layers (HTL) can be added using, for example, spin casting, ink jetting, doctor blading, spray casting, dip coating, vapor depositing, or any other known deposition method.

The HTLs can be formed as films from, for example, PEDOT, PEDOT/PSS or TBD, or NPB, or PLEXCOR® OC inks (Plextronics, Pittsburgh, Pa.).

The thickness of the HTL or HIL layer can be, for example, from about 10 nm to about 300 nm thick, or from 30 nm to 60 nm, 60 nm to 100 nm, or 100 nm to 200 nm. The film then can be optionally dried/annealed at, for example, 40° C. to 200° C., or 110° C. to 200° C. for 1 min to an hour, optionally in an inert atmosphere.

Active layer thickness can be, for example, about 50 nm to about 250 nm, including for an OPV device.

The active layer can be formulated from a mixture of n-type and p-type materials. The n- and p-type materials can be mixed in a ratio of, for example, from about 0.1 to 4.0 (p-type) to about 1 (n-type) based on a weight, or from about 1.1 to about 3.0 (p-type) to about 1 (n-type) or from about 1.1 to about 1.5 (p-type) to about 1 (n-type). The amount of each type of material or the ratio between the two types of components can be varied for the particular application.

The active layer can be then deposited by spin casting, ink jetting, doctor blading, spray casting, dip coating, vapor depositing, or any other known deposition method, on top of the HTL or HIL film. The film is then optionally thermally annealed at, for example, about 40 to about 250° C., or from about 150 to 180° C., for about 10 min to an hour in an inert atmosphere. Solvent annealing can be also carried out as needed.

A cathode layer can be added to the device, generally using, for example, thermal evaporation of one or more metals. For example, a 1 to 15 nm Ca layer is thermally evaporated onto the active layer through a shadow mask, followed by deposition of a 10 to 300 nm Al layer. A variety of layers can be included between the cathode and the active layer of a solar cell or the emissive layer of an OLED. These layers are generally referred to as electron transport layers (ETL), electron injection layers (EIL), hole blocking layers (HBL) and/or interlayers.

In some embodiments, an optional interlayer may be included between the active layer and the cathode, and/or between the HTL or HIL and the active layer. This interlayer can be, for example, from 0.5 nm to about 100 nm, or from about 1 to 3 nm, thick. The interlayer can comprise an electron conditioning, a hole blocking, or an extraction material, such as LiF, BCP, Li/Al, bathocuprine, fullerenes or fullerene derivatives, such as C60, C70, C84, or C60:Mg and other fullerenes and fullerene derivatives discussed herein.

Electron transport layers can be used in, for example, solar cell devices. See, for example, U.S. patent application No. 61/116,963 filed Nov. 21, 2008.

Interfacial modification layers can be used as described in, for example, PCT/US2009/006236 filed Nov. 20, 2009 (Plextronics, Inc.). The interfacial modification layer can comprise, for example, an organic semiconductor which is doped by, for example, a metal (e.g., BPhen:Yb). The interfacial modification layer can be prepared by vacuum deposition methods. It can have a thickness of, for example, 3 nm to 25 nm, or 5 nm to 15 nm. An Al layer can be disposed on top.

The devices can be then encapsulated using a glass cover slip sealed with a curable glue, or in other epoxy or plastic coatings. Cavity glass with a getter/desiccant may also be used.

In addition, the active layer can comprise additional ingredients including, for example, surfactants, dispersants, oxygen and water scavengers.

The active layer can comprise multiple layers or be multi-layered.

The active layer composition can be formed from an ink comprising a mixture as a film. Films and devices can be annealed before use and testing. Thermal annealing and solvent annealing can be carried out.

Inverted solar cells can be made. See, for example, Chen et al. *Advanced Materials,* 2009, 21, 1-16. Tandem solar cells can be made. See, for example, Yang, Y. et al. *Adv. Mater.,* 2010, 22, 380.

Device Testing

Known solar cell parameters can be measured including for example $J_{SC}$ (mA/cm$^2$) and Voc (V) and fill factor (FF) and power conversion efficiency (%, PCE) by methods known in the art. See for example Hoppe article cited above and references cited therein.

Oriel Solar Simulators can be used to determine PV properties including, for example, FF, Jsc, Voc, and efficiencies. The simulator can be calibrated by methods known in the art including, for example, calibration with a KG5-Si reference cell. External quantum efficiency (EQE) can be measured.

Other properties for the inks, films, and devices can be measured by methods known in the art.

Power conversion efficiency (PCE) can be, for example, at least about 1%, or at least about 2%, or at least about 3%, or at least about 4%, or at least about 5%, or at least about 6%, or at least about 7%, or at least about 8%, or higher.

Fill factor, which can be expressed as a number between 0 and 1, or a percentage between 0 and 100%, can be, for example, at least about 0.4 (40%), or at least about 0.5 (50%), or at least about 0.6, or at least about 0.7, or at least about 0.8, or at least about 0.9 or higher.

Open circuit voltage ($V_{OC}$) in V can be, for example, at least about 0.3, or at least about 0.4, or at least about 0.5, or at least about 0.6 V, or at least about 0.7 V, or at least about 0.8 V, or at least about 0.9 V, or at least about 1.0 V, or at least about 1.1 V, or at least about 1.2 V, or at least about 1.3 V, or higher.

Short circuit current ($J_{SC}$) can be, for example, at least about 0.5, or at least about 0.6, or at least about 0.7, or at least about 0.8, or at least about 0.9, or at least about 1.0, or at least about 2.0, or at least about 3.0, or at least about 4.0, or at least about 5.0, or at least about 10.0, or higher (mA/cm$^2$).

Energy Harvesting

In addition, devices and applications can be made and carried out in energy harvesting (EH). Energy harvesting is an indoor application of photovoltaic technology, whereby an EH device harnesses ambient light, typically fluorescent office lighting, for energy storage or direct use for a wide variety of low power applications. For example, a typical office environment can have light levels of about 1000 LUX, or about 0.5% (0.5 mW/cm^2) of the incident radiant energy of 1 sun. This represents the total amount of energy that can be harvested in these environments and high efficiency photovoltaic technology, suited to these light levels are important for leveraging novel applications and can be a replacement for coin-cell batteries (or equivalent). Typical outdoor solar technology, such as mc-Si c-Si, have low performance at indoor lighting levels due to a high amount of Voltage loss. Organic PV and a-Si are well suited to low light levels and OPV can be a more cost effective solution vs. a-Si and thus can be used in EH technology.

Polymers can be designed to exhibit a 'flat' response with decreasing light levels and represent a novel high-performance technology of indoor EH applications. Typical device stacks for EH applications are very similar to their outdoor solar analogs and a typical configuration is ITO/ZnO/conjugated polymer:PCBM[C60]/HTL/Ag.

Devices can be tested at 1000 LUX and one can determine the power density at this standard luminance level. In addition, one can measure devices at a variety of light intensities to understand how device parameters change with changes in ambient light level. One can also measure leakage current at reverse bias to help understand the diode quality as poor diode quality can result in lower performance at lower and lower light levels.

Photodetection

In addition, organic photodetection (OPD) is an application of PV technology where a circuit can be controlled by the presence or absence of radiant energy impinging on the said circuit, which contains a photosensitive device. The use of organic photodetectors offers an advantage of cost and integration that may not be possible with incumbent technology, namely a-Si.

OPD devices can be fabricated very similarly to a solar OPV device and a typical configuration is: ITO/HTL/conjugated polymer:Fullerene n-type/Cathode, where the cathode can be Ca/Al, or organic small molecule, doped with a metal, or organic material and capped with a metal such as Aluminum.

There are four quadrants of a current voltage plot which are defined by positive and negative current and voltage (I=+c/−v, II=+c/+v (OLED), III=−c/−v (OPD), IV=−c/+v (OPV)). OLED devices operate in quadrant II, OPVs in quadrant IV and OPDs in quadrant III.

For OPD the product of current and voltages are always positive thus this is a device which requires power input. The input power is provided to the OPD circuit and when the OPV cell is exposed to light, a massive gain (several decades, up to >10^4) in current can occur. This provides a 'gate' which allows the circuit to differentiate between light (on) and dark (off) states, thus allowing for photodetection.

For OPD technology, key parameters include 1) current density (expressed as mA/cm^2 and higher is better) at a negative voltage (at typically −1 or −2 V) and 2) the noise floor in the dark state, typically expressed as a current density (nA/cm^2) and the lower the better. Parameter #1 is proportional to the quantum efficiency of the device and devices which are most efficient at generating current with the input radiant energy are best. For #2, device design is necessary to reduce the leakage current (or noise floor) and the photoactive layer materials should have as low a carrier density in the off state as possible, ie not doped.

Materials described herein can offer high quantum efficiency, low doping due to deep HOMO, and air processibility that is amenable to rapid OPD device development.

Part IV

Working Examples

Additional embodiments are provided in the following working examples.
Synthesis: Monomers and Polymers The following synthetic examples are illustrative and not intended to be limiting. Unless specified, reactions were conducted under prepurified nitrogen or argon, using oven-dried and/or flame-dried glassware. Ice/water, dry ice/acetone were used for 0° and −78° C. baths, respectively. Commercial chemicals were purchased from Aldrich Chemical Co., Inc. and used without further purification. Titration of the Grignard/organolithium reagents was performed following the procedure described by Love, et al. *J. Org. Chem.* 1999, 64, 3755.
Materials.

Syntheses of the following materials were adapted from the published procedures:
[4,8-bis(3-ethylheptyl)-6-trimethylstannyl-thieno[2,3-f]benzothiophen-2-yl]-trimethyl-stannane [Plextronics Patent Application on *Organic Electronic Devices and Polymers, Including Photovoltaic Cells and Diketone-Based Polymers*]

4,8-diethylhexyloxybenzo[1,2-b;3,4-b]dithiophene [Lit. Ref.: Hou et al., *Macromolecules* 2008, 41, 6012];
4,7-dibromo-benzo[1,2,5]thiadiazole [Lit. Ref.; Hou et al., *Mater. Chem.* 2002, 10, 2887];
1,3-Dibromo-5-(2-ethylhexyl)thieno[3,4-c]pyrrole-4,6-dione; was received from Acoris, Inc. (synthesis was adapted from Zhang et al., J. M. *J. Am. Chem. Soc.* 1997, 119, 5065).

General synthesis of alkynes from aldehydes was adapted from Roth, et al., *Synthesis, Journal of Synthetic Organic Chemistry*, 2004, 1, 59

Example 1

Synthesis of 5,6-difluorobenzo[c][1,2,5]thiadiazole

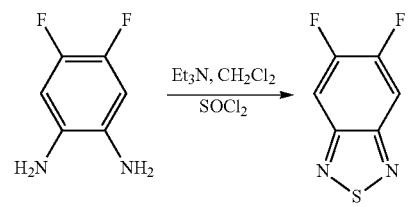

A dry 1000 mL round bottom flask, equipped with a condenser, was purged with nitrogen and charged with 4,5-difluorobenzene-1,2-diamine (10 g, 0.069 mol), 400 mL of anhydrous methylene chloride ($CH_2Cl_2$), and triethylamine (38.7 mL, 0.28 mol). The reaction flask was cooled to 0° C. and thionyl chloride (30.2 mL, 0.41 mol) was added dropwise. The ice bath was removed and the mixture was heated to reflux for 1 hour. Completion of reaction was monitored by GC-MS. As the reaction was completed, the mixture was concentrated down, quenched with cold water, and extracted with $CH_2Cl_2$ (3×300 mL). The organic phase was dried over anhydrous MgSO4, filtered, and concentrated down. The final product was purified using column chromatography on silica gel with hexanes/ethyl acetate (80:20) gradient to yield white crystalline solid (6.3 g, 53%). Spectral data: $^1$H NMR (300 MHz, $CDCl_3$): $\delta_H$ 7.75 (t, 2H).

Example 2

Synthesis of 4,7-dibromo-5,6-difluorobenzo[c][1,2,5]thiadiazole

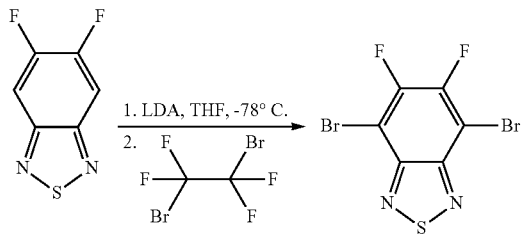

A dry 250-mL three-neck round bottom flask was flushed with $N_2$ and was charged with diisopropylamine (0.51 mL, 3.62 mmol) and anhydrous THF (4.0 mL), both of which were added via a deoxygenated syringe. The reaction flask was cooled to 0° C. and a 2.5 M solution of n-butyllithium (1.45 mL, 3.62 mmol) was added drop-wise via a deoxygenated syringe. After 20 minutes of stirring at 0° C., the solution was chilled to −76° C. (acetone/dry ice bath), and stirring continued for 5 minutes. Chilled to −76° C. anhydrous THF (72 mL) was added to the reaction flask via a deoxygenated syringe to achieve concentration of 0.05 M, followed by a drop-wise addition of 1.45 M solution of 5,6-difluorobenzo[c][1,2,5]thiadiazole (0.25 g, 1.45 mmol) in anhydrous THF (1 mL). The reaction mixture was stirred for 6 hours at −76° C. 1,2-Dibromotetrafluoroethane (0.43 mL, 3.62 mmol) was added drop-wise and the mixture was allowed to stir for another 15 minutes at −76° C. The mixture was quenched with 10% HCl (aq) and the water cooling bath was removed. The aqueous layer was separated and extracted with chloroform (3×50 mL). The collected organic phase was dried over anhydrous MgSO$_4$. After filtration, the solvent was removed by evaporation under reduced pressure. The crude product was purified using column chromatography on silica gel with hexane, followed by double recrystallization from hexanes and THF/methanol/water, respectively. The compound was dried under vacuum to yield 0.15 g (30%) of white solid.

Example 3

Synthesis of random copolymers based on 5,6-difluorobenzo[c][1,2,5]thiadiazole

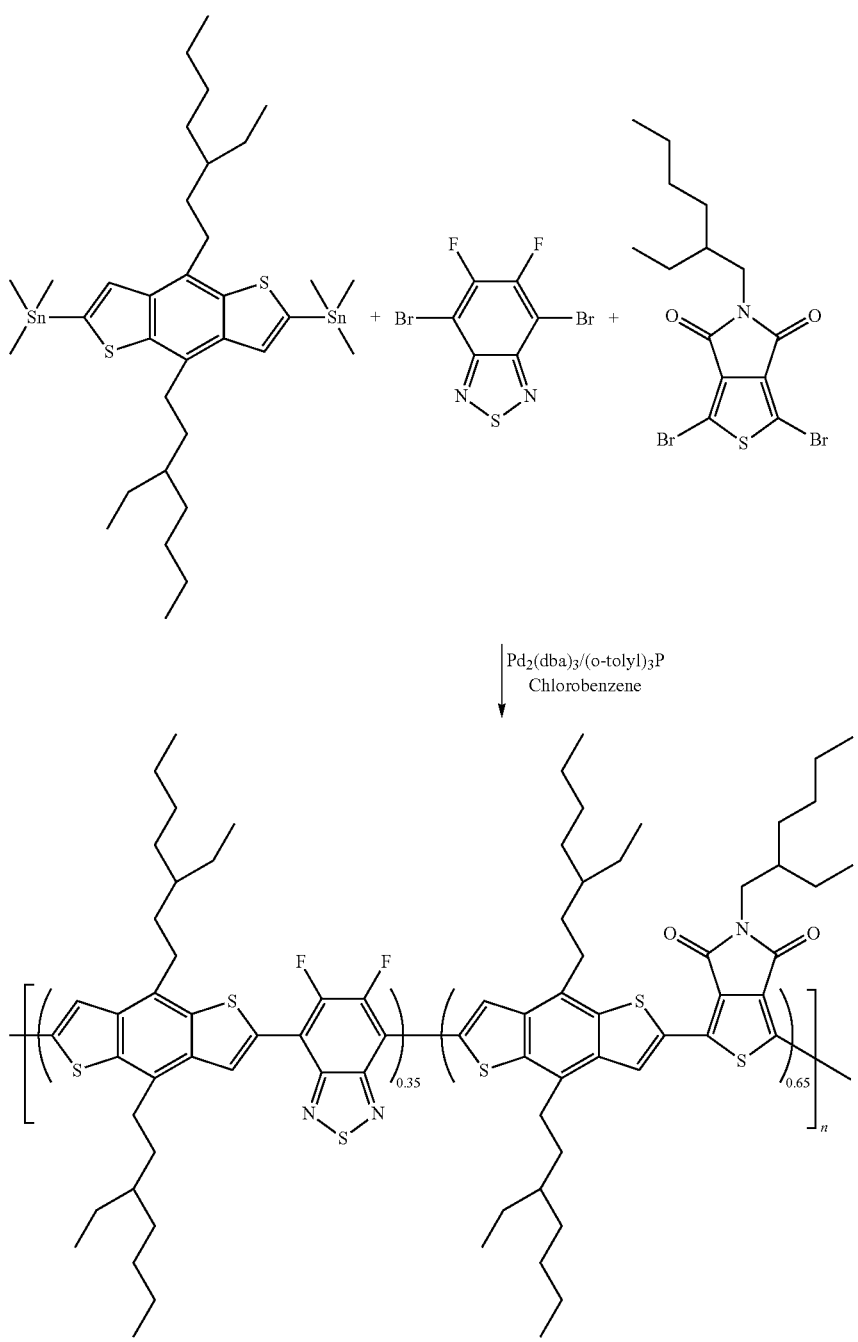

In a glove box, (4,8-bis(3-ethylheptyl)benzo[1,2-b:4,5-b']dithiophene-2,6-diyl)bis(trimethylstannane) (0.27 g, 0.36 mmol), 4,7-dibromo-5,6-difluorobenzo[c][1,2,5]thiadiazole (0.041 g, 0.12 mmol), 1,3-dibromo-5-(2-ethylhexyl)-4H-thieno[2,4-c]pyrrole-4,6(5H)-dione (0.098 g, 0.23 mmol), tris(dibenzylideneacetone)dipalladium(0) [Pd$_2$(dba)$_3$] (8.1 mg, 0.010 mmol) and tris(o-tolyl)phosphine (11 mg, 0.036 mmol) [(o-tolyl)$_3$P] were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a preheated to 110° C. oil bath and left stirring under an argon stream for 3 hours, cooled down to ambient temperature and another portions of Pd$_2$(dba)$_3$ and (o-tolyl)$_3$P (8.1 mg and 11 mg, respectively) in 2 mL of deoxygenated chlorobenzene were added. The mixture was evacuated and refilled with argon five times, finally immersed into a preheated to 110° C. oil bath, and left stirring under an argon stream for 2 days. After cooling to room temperature, 30 mL of MTBE/methanol (50:50 mixture) were added to the reaction flask. The polymer was collected via filtration and purified by consecutive Soxhlet extractions in sequence with methanol, MTBE, hexane, and chloroform. The chloroform solution was passed through a bed of thiol-bound silica gel to remove catalyst and/or other small molecules residuals, and solvent was removed under vacuum to yield polymer. The polymer was re-dissolved in a small amount of chloroform, re-precipitated in the mixture of IPA, water and methanol, isolated, and dried to yield a brown-copper colored polymer (0.18 g). Molecular weight was determined by GPC in chlorobenzene (1 mL/min at 80° C.) vs. polystyrene standards: $M_n$=44,000, $M_w$=105,800, PDI=2.4.

Example 4

(Comparative) Poly{(4,8-bis(3-ethylheptyl)thieno[2,3-f]benzothiophene-alt-(5-(2-ethylhexyl)thieno[3,4-c]pyrrole-4,6-dione)-ran-(4,8-bis(3-ethylheptyl)thieno[2,3-f]benzothiophene-alt-4,7-[2,1,3-benzothiadiazole])}

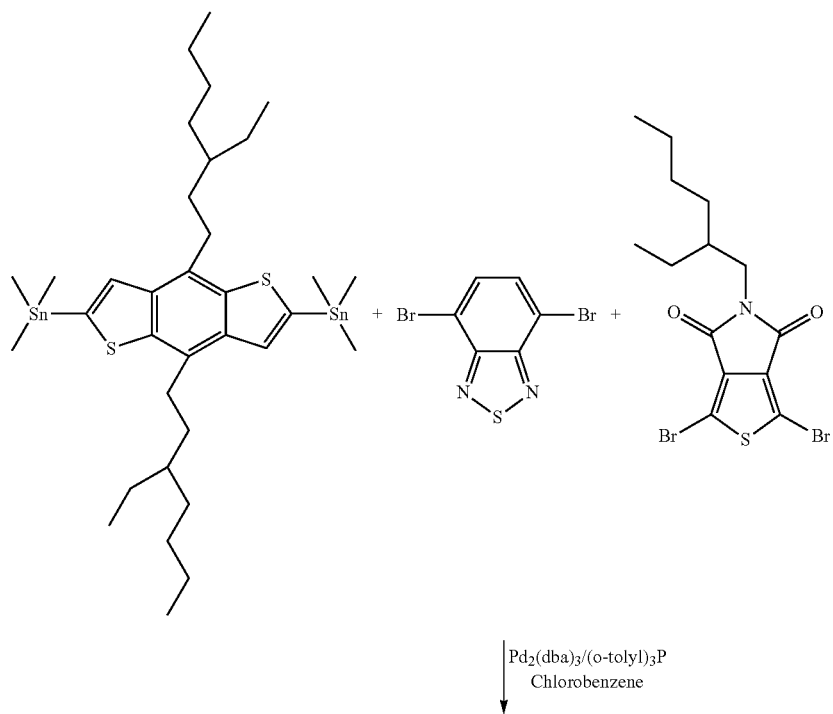

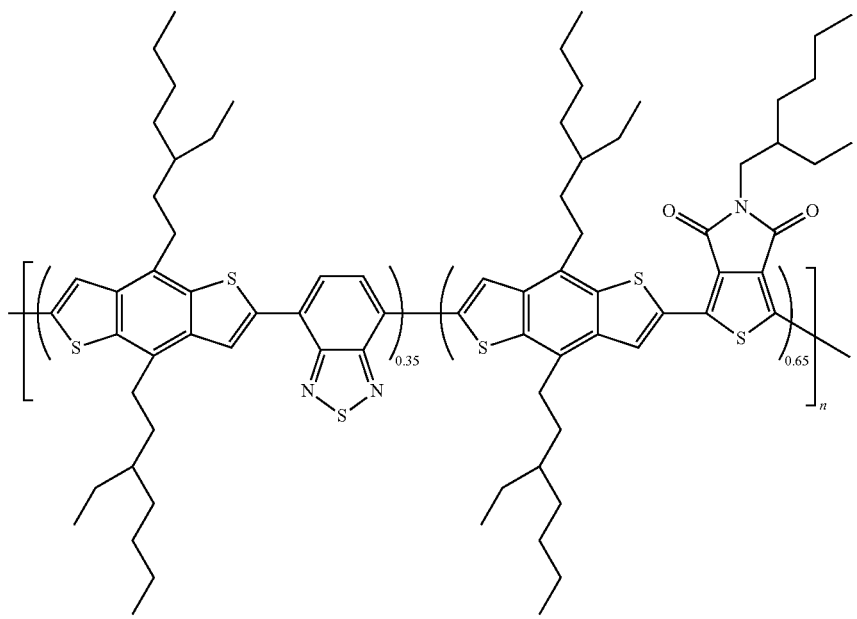

In a glove box, [4,8-bis(3-ethylheptyl)-6-trimethylstannyl-thieno[2,3-f]benzothiophen-2-yl]-trimethyl-stannane (0.30 g, 0.39 mmol), 1,3-dibromo-5-(2-ethylhexyl)thieno[3,4-c]pyrrole-4,6-dione (0.11 g, 0.25 mmol), 4,7-dibromo-2,1,3-benzothiadiazole (0.040 g, 0.14 mmol), tris(dibenzylideneacetone)dipalladium(0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 3 hours and another portion of $Pd_2(dba)_3$/(o-tolyl)$_3$P was added. The polymerization was left to stir at 110° C. for 48 hours, cooled to 40° C., and 30 mL of MTBE were added to the reaction mixture under vigorous stirring to induce precipitation. The final mixture was poured into 200 mL of MTBE and the polymer was collected via filtration. The polymer was purified by consecutive Soxhlet extractions in sequence with MTBE, acetone, hexane, and chloroform. The chloroform fraction was passed through celite and silica gel to remove catalyst residuals, solvent was removed under vacuum to yield a brown-copper colored polymer that was redissolved in chloroform, precipitated in methanol:IPA:water mixture, and collected via filtration (80%). Molecular weight was determined by GPC in chlorobenzene (1 mL/min at 80° C.) vs. polystyrene standards: $M_n$=23,300, $M_w$=83,100, PDI=3.6.

Example 5

2,6-bis(trimethyltin)-4,8-diethylhexyloxybenzo[1,2-b;3,4-b]dithiophene

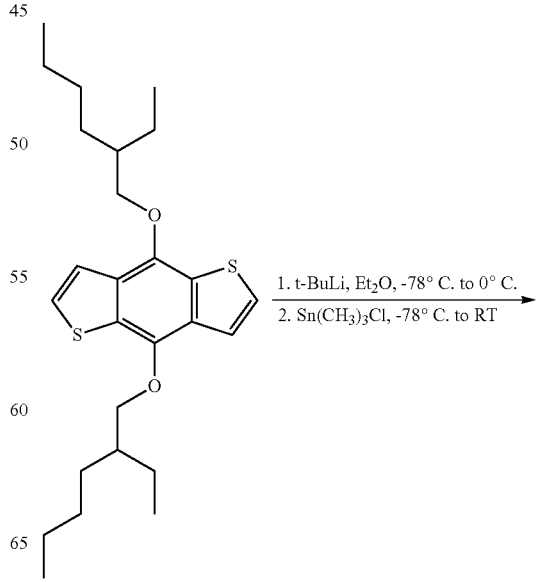

-continued

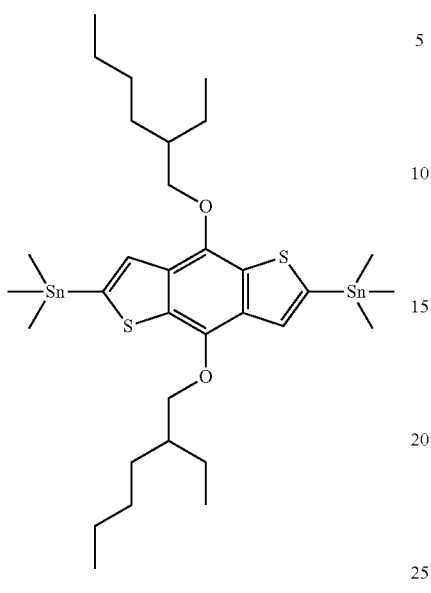

A dry 500-mL three-neck flask was flushed with N₂ and was charged with 4,8-diethylhexyloxybenzo[1,2-b;3,4-b]dithiophene (6.9 g, 0.015 mol) and diethyl ether (Et₂O) (150 mL, 0.1 M) via deoxygenated syringe. The reaction flask was cooled to −78° C. and a 1.7 M solution of tert-butyllithium in hexanes (23 mL, 0.038 mol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (39 mL, 0.038 mol) was added to the reaction flask dropwise and stirring continued for 1 hour at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with hexanes (150 mL) three times. The combined organic layer was washed with water two times and dried over anhydrous magnesium sulfate (MgSO₄). After the product was filtered, the solvent was removed by rotary evaporation. The crude product was purified by recrystallization three times from THF/methanol to yield white crystalline solid (7.3 g, 61%).

Spectral data: ¹H NMR (300 MHz, CDCl₃): $\delta_H$ 7.15 (s, 2H), 4.18 (d, 4H), 1.81 (m, 4H), 1.60 (m, 14H), 1.08 (t, 6H), 0.95 (t, 6H), 0.45 (s, 18H).

Example 6 (Comparative)

Poly{2,6'-4,8-diethylhexyloxybenzo[1,2-b;3,4-b]dithiophene-alt-(5-(2-ethylhexyl)thieno[3,4-c]pyrrole-4,6-dione}

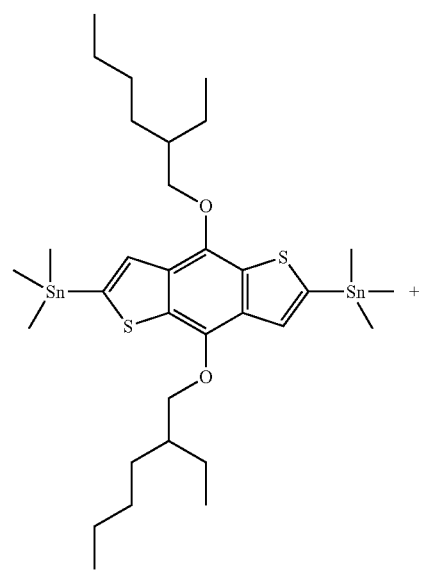

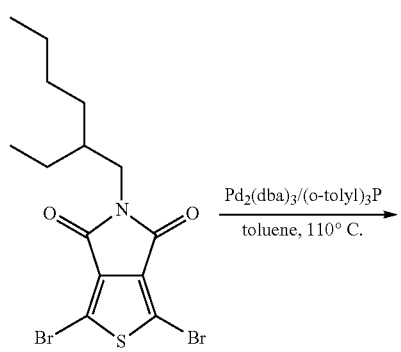

-continued

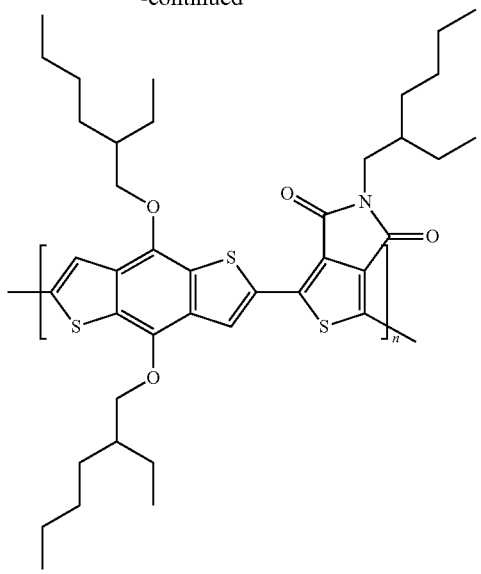

In a glove box, 2,6-bis(trimethyltin)-4,8-diethylhexyloxybenzo[1,2-b;3,4-b]dithiophene (0.4 g, 0.52 mmol), 1,3-dibromo-5-(2-ethylhexyl)thieno[3,4-c]pyrrole-4,6-dione (0.22 g, 0.52 mmol), tris(dibenzylideneacetone)dipalladium(0) (0.012 g, 0.013 mmol) and tris(o-tolyl)phosphine (0.016 g, 0.052 mmol) were weighted out into a flame dried 50 mL Schlenk flask. Reaction flask was removed from the glove box and 6 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.18 g, 50%). Molecular weight was determined by GPC in 1,3,5-trichlorobenzene (1 mL/min at 150° C.) vs. polystyrene standards: $M_n$=24,700, $M_w$=49,100, PDI=2.0.

Fabrication of Solar Cell Devices Using Polymers and Fullerene Acceptors

Inks were formulated with a fullerene derivative acceptor and solvent.

Indium tin oxide ("ITO") coated glass substrates were purchased from Thin Film Devices ("TFD", Anaheim, Calif.). These substrates were cleaned in a Class 10,000 clean room by sonicating for 20 min in a soap solution, followed by 20 min of sonication in water, 20 min of sonication in acetone and 20 min of sonication in IPA. Finally the substrates were exposed to UV ozone (300 W) for 10 min. After cleaning, each substrate was then coated with a ~40 nm thick layer of Plexcore HIL (2052) by spin coating for 3 seconds at 350 rpm in air, followed by a 1 minute at 1200 rpm. The devices were then transferred to a $N_2$ atmosphere glovebox and annealed on a hot plate at 110° C. for 30 min.

The active layer was then spin-coated on top of the Plexcore HIL layer on a Headway spinner at spin speeds ranging from 300-1000 rpm to obtain the required active layer thickness. The active layer films were allowed to dry in the glovebox. Finally, the cathode was vapor deposited from a base pressure of ~7×10$^{-7}$. In some of the following working examples, the cathode for the devices was either a bilayer of Ca (10 nm) and Al (90 nm) or Bphen/Yb (10 nm) and Al (90 nm). The Ca and Al were deposited at rates of 0.3 Å/s and 3 Å/s, respectively, and Bphen and Yb were deposited at rates of 1 Å/s and 0.1 Å/s, respectively. The devices were then encapsulated via a glass cover slip (blanket) encapsulation sealed with EPO-TEK OG112-4 UV curable glue. The encapsulated device was cured under UV irradiation (80 mW/cm$^2$) for 4 minutes and tested as follows.

The photovoltaic characteristics of devices under white light exposure (Air Mass 1.5 Global Filter) were measured using a system equipped with a Keithley 2400 source meter and an Oriel 300 W Solar Simulator based on a Xe lamp with output intensity of 100 mW/cm$^2$ (AM1.5G). The light intensity was set using an NREL-certified Si-KG5 silicon photodiode.

Power Conversion Efficiency Determinations

Devices prepared as described above were tested using an Oriel Solar Simulator and the voltage was swept from reverse to forward bias. From the resulting current that was measured, the power conversion efficiency of each device was determined. Data for each device are summarized in Tables 1, 2, and 3, as well as relevant processing parameters for each device.

UV-Vis Data:

FIG. 1. Comparison of normalized UV-Vis absorption profiles of solid-state benzobithiophene-based alternating Donor-Acceptor (D-A 1) copolymers: a) with 5-(2-ethylhexyl)thieno[3,4-c]pyrrole-4,6-dione as one acceptor in a (D-A) copolymer architecture (Synthetic Example 6; black); b) with 5-(2-ethylhexyl)thieno[3,4-c]pyrrole-4,6-dione and fluorinated-benzothiadiazole as two acceptors in a (D-A1-D-A2) copolymer architecture (Synthetic Example 3; blue); and c) with 5-(2-ethylhexyl)thieno[3,4-c]pyrrole-4,6-dione and unfluorinated-benzothiadiazole as two acceptors in a (D-A1-D-A3) copolymer architecture (Synthetic example 4; red).

Figure 2A:
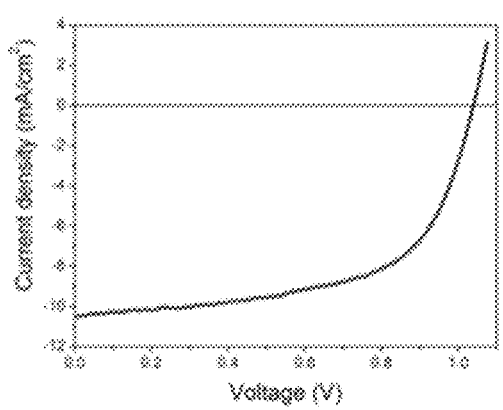
FIG. 2. (A) Current-Voltage (I-V) dependance for D-A polymer (plot on the left); (B) Current-Voltage (I-V) dependance in dark (plot on the right).
Figure 2B:
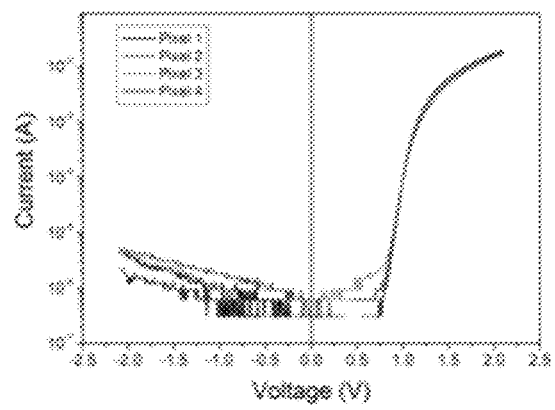

Materials properties (e.g., processability, solubility, planarity/order and/or band gap) of D-A polymers disclosed in this invention can be tuned by varying molar composition and/or functionality of starting materials OPV Data:

FIG. 2. a) Current-Voltage (I-V) dependance for D-A polymer (Synthetic Example 3) and C70PCBM (device fabrication/formulation details and OPV characteristics are listed in Table 1, seventh entry with OPV efficiency of 6.51%) under 1SUN illumination (plot on the left); b) Current-Voltage (I-V) dependance in dark (plot on the right).

TABLE 1

Results for photovoltaic performance of single layer OPVs based on Donor-Acceptor polymer comprising fluorinated-benzothiadiazole (Synthetic Example #3) and C70PCBM as an n-type acceptor: solvent effect on performance [ODCB vs. TCB:ODCB (50:50) blend].

| Device | P-type | P-type mg/ml | p/n ratio | Solvent system[1] | Ink processing temp (° C.) | HIL | Spin Speed | Thickness | Voc avg | Jsc avg | FF avg | E % avg |
|---|---|---|---|---|---|---|---|---|---|---|---|---|
| 1 | Example 3 | 7 | 1/2 | ODCB | 75 | A | 400 | 89 | 1.03 | 9.71 | 0.509 | 5.09 |
| 2 | Example 3 | 7 | 1/2 | ODCB | 75 | A | 500 | 64 | 1.04 | 10.8 | 0.543 | 6.07 |
| 3 | Example 3 | 7 | 1/2 | ODCB | 75 | A | 650 | 60 | 1.04 | 10.1 | 0.55. | 5.77 |
| 4 | Example 3 | 7 | 1/2 | ODCB | 75 | A | 600 | 62 | 1.04 | 10.2 | 0.544 | 5.80 |
| 5 | Example 3 | 7 | 1/2 | TCB-ODCB | 75 | A | 500 | 63 | 1.05 | 10.6 | 0.585 | 6.48 |
| 6 | Example 3 | 7 | 1/2 | TCB-ODCB | 75 | A | 600 | 57 | 1.05 | 10.5 | 0.586 | 6.43 |
| 7 | Example 3 | 7 | 1/2 | TCB-ODCB | 75 | A | 650 | na | 1.05 | 10.5 | 0.592 | 6.51 |
| 8 | Example 3 | 7 | 1/2 | TCB-ODCB | 75 | A | 550 | 57 | 1.05 | 10.4 | 0.585 | 6.37 |
| 9 | PV2000 | 15.5 | | ODCB | 70/RT | A | 450 | | 1.05 | | | |

| Ramp speed (rpm/s) or ACL | Spread time (s) | Spread speed (rpm) | Spin time (s) | Spin Temp deg C. |
|---|---|---|---|---|
| 1000 | 3 | 300 | 360 | 75 |

[1]TCB—trichlorobenzene; ODCB—o-dichlorobenzene;

Note:
HIL A is a Plexcore HIL ink formulation comprising 96.860 parts water; 2.826 parts Nafion (sulfonated perfluorinated copolymer); and 0.314 parts sulfonated polythiophene as described in PCT publication WO 2008/073149.
*PV2000 Plexcore OPV ink utilizing poly(3-hexylthiophene) (P3HT) as a donor polymer and fullerene acceptors described in US Patent Publication 2008/0319207.

TABLE 2

Results for photovoltaic performance of single layer OPVs based on Donor-Acceptor polymer comprising fluorinated-benzothiadiazole (Synthetic Example #3) and C70PCBM as an n-type acceptor: comparison between different p:n ratio blends.

| Device | P-type | P-type mg/ml | p/n ratio | Solvent system[1] | Ink processing temp (° C.) | HIL | Spin Speed | Thickness [nm] | Voc avg [V] | Jsc avg [mA/cm$^2$] | FF avg | E % avg | Best |
|---|---|---|---|---|---|---|---|---|---|---|---|---|---|
| 1 | Example 3 | 7 | 1/1.5 | TCB-ODCB | 100 | A | 1000 | 48 | 1.068 | 9.4332 | 0.52784 | 5.32 | 5.55 |
| 2 | Example 3 | 7 | 1/1.5 | TCB-ODCB | 100 | A | 850 | 47 | 1.0665 | 10.12 | 0.52125 | 5.63 | 6.62 |
| 3 | Example 3 | 7 | 1/2.5 | TCB-ODCB | 100 | A | 550 | 64 | 1.0588 | 10.504 | 0.5963 | 6.63 | 6.72 |
| 4 | Example 3 | 7 | 1/2.5 | TCB-ODCB | 100 | A | 475 | 61 | 1.06275 | 10.5525 | 0.584775 | 6.56 | 6.66 |
| 5 | Example 3 | 7 | 1/2 | TCB-ODCB | 100 | A | 600 | 57 | 1.06675 | 10.49 | 0.5846 | 6.54 | 6.61 |
| 6 | Example 3 | 7 | 1/2 | TCB-ODCB | 100 | A | 650 | 60 | 1.067 | 10.3825 | 0.580375 | 6.43 | 6.65 |
| 7 | Example 3 | 7 | 1/2 | TCB-ODCB | 100 | A | 675 | 53 | 1.066 | 10.2325 | 0.590575 | 6.44 | 6.66 |
| 8 | Example 3 | 7 | 1/2 | TCB-ODCB | 100 | A | 700 | 51 | 1.059 | 9.18475 | 0.584525 | 6.26 | 6.66 |
| 9 | PV2000 | 15.5 | | ODCB | 70/RT | A | 450 | | | | | | |

[1]TCB—trichlorobenzene; ODCB—o-dichlorobenzene;

Note:
HIL A is a Plexcore HIL ink formulation comprising 96.860 parts water; 2.826 parts Nafion (sulfonated perfluorinated copolymer); and 0.314 parts sulfonated polythiophene as described in PCT publication WO 2008/073149.

TABLE 3

Results for photovoltaic performance of single layer OPVs based on Donor-Acceptor polymers comprising fluorinated-benzothiadiazole (Synthetic Example #3) vs. unfluorinated counterpart (Synthetic Example #4) and C70PCBM as an n-type acceptor.

| Device | P-type | P-type mg/ml | p/n ratio | Solvent system[1] | Ink processing temp (° C.) | HIL | Spin Speed | Thickness | Voc avg | Jsc avg | FF avg | E % avg | Best |
|---|---|---|---|---|---|---|---|---|---|---|---|---|---|
| 1 | Example 4 | 7 | 1/2 | ODCB | 75/75 | A | 500 | 90 | 0.96 | 8.79 | 0.45 | 3.80% | 3.85% |
| 2 | Example 4 | 7 | 1/2 | ODCB: o-xylene (75:25) | RT/RT | A | 650 | 79 | 0.97 | 10.25 | 0.55 | 5.43% | 5.65% |
| 3 | Example 4 | 7 | 1/2 | ODCB: o-xylene (75:25) | RT/RT | A | 750 | 69 | 0.97 | 9.89 | 0.55 | 5.28% | 5.40% |
| 4 | Example 4 | 7 | 1/2 | ODCB: o-xylene (75:25) | RT/RT | A | 850 | 65 | 0.96 | 9.61 | 0.54 | 5.03% | 5.19% |
| 5 | Example 3 | 7 | 1/2 | ODCB | 75/75 | A | 500 | 116 | 0.97 | 7.95 | 0.50 | 3.87% | 3.92% |
| 6 | Example 3 | 7 | 1/2 | ODCB: o-xylene (75:25) | RT/RT | A | 1000 | 74 | 1.04 | 8.89 | 0.60 | 5.48% | 5.50% |
| 7 | Example 3 | 7 | 1/2 | ODCB: o-xylene (75:25) | RT/RT | A | 900 | 87 | 1.03 | 8.76 | 0.57 | 5.14% | 5.17% |
| 8 | Example 3 | 7 | 1/2 | ODCB: o-xylene (75:25) | RT/RT | A | 1100 | 94 | 1.03 | 8.72 | 0.57 | 5.09% | 5.16% |

[1]ODCB—o-dichlorobenzene;

Note:
HIL A is a Plexcore HIL ink formulation comprising 96.860 parts water; 2.826 parts Nafion (sulfonated perfluorinated copolymer); and 0.314 parts sulfonated polythiophene as described in PCT publication WO 2008/073149.

Calculations

Embodiments can be prepared which can increase the electron affinity of the acceptor. This deepening of the acceptor LUMO (e.g., deeper than −2.6 eV for a 5,6-difluorobenzo[c][1,2,5]thiadiazole counterpart versus −2.35 eV for benzo[c][1,2,5]thiadiazole, see Table 1) providing for donor-acceptor polymers with smaller bandgap and thus, a broader absorption of solar spectrum allowing for higher efficiency. Calculations for Acceptor LUMOs using a density functional method, B3LYP with a 6-31 G(d) basis set demonstrate that each fluorine deepens the LUMO for benzothiadiazole by approximately 125 meV.

TABLE 1

Summary of calculated HOMO and LUMO values for acceptors.

| Acceptor | HOMO | LUMO |
|---|---|---|
| 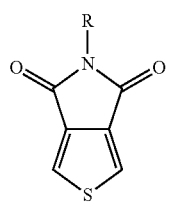 | −7.37 | −1.87 |

TABLE 1-continued

Summary of calculated HOMO and LUMO values for acceptors.

| Acceptor | HOMO | LUMO |
|---|---|---|
| (5,6-difluoroquinoxaline structure) | −7.04 | −2.19 |
| (2,3-difluoroquinoxaline structure) | −7.02 | −2.16 |
| (5,6-difluorobenzo[c][1,2,5]thiadiazole structure) | −6.95 | −2.6 |

TABLE 1-continued

Summary of calculated HOMO and LUMO values for acceptors.

| Acceptor | HOMO | LUMO |
|---|---|---|
| 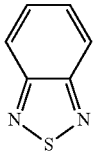 | −6.61 | −2.35 |
| 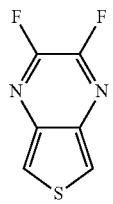 [SMILES: Fc1nc2cscc2nc1F] | −6.59 | −2.46 |
| 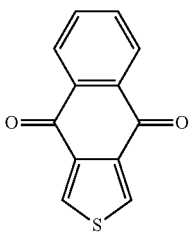 [SMILES: O=C1c2ccccc2C(=O)c2cscc21] | −6.87 | −2.54 |
| 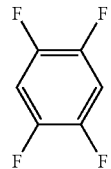 | −6.78 | −0.88 |
| 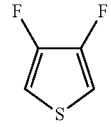 | −6.76 | −0.61 |
| 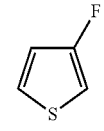 | −6.43 | −0.44 |
| 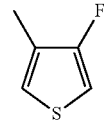 | −6.32 | −0.37 |

Surprisingly, some of these electron deficient acceptors also provide embodiments which can be used with electron rich donor-building blocks to deepen HOMO (e.g., shift lower by about 0.4 eV). This can provide for a higher Voc, as the latter correlates with the difference between HOMO and LUMO levels of donor and acceptor counterparts, such as fullerene and their derivatives, respectively, thus resulting in increased OPV efficiency.

What is claimed is:

1. A composition comprising at least one donor-acceptor copolymer, wherein the donor of the donor-acceptor copolymer comprises at least one fused ring system, wherein the first acceptor moiety of the donor-acceptor copolymer is represented by:

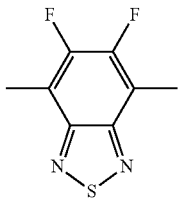

(II)

and wherein the donor-acceptor copolymer further comprises at least one second acceptor moiety of the copolymer different from the first acceptor moiety of the copolymer which is represented by (VIII):

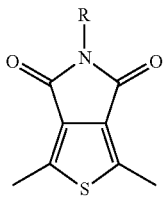

(VIII)

wherein R is a solubilizing group.

2. The composition of claim 1, wherein the donor comprises a benzodithiophene moiety.

3. The composition of claim 1, wherein the number average molecular weight of the copolymer is at least 10,000.

4. The composition of claim 1, wherein the copolymer is soluble and has a molecular weight of at least 10,000.

5. The composition of claim 1, wherein the donor moiety comprises at least one thiophene ring.

6. The composition of claim 1, wherein the donor moiety comprises at least two thiophene rings.

7. The composition of claim 1, wherein the donor moiety comprises at least three fused rings.

8. The composition according to claim 1, wherein the at least one donor-acceptor copolymer comprises phthalimide units and head-to-head substituted biheteroaryl units in an amount less than 10 mole percent.

9. The composition according to claim 8, wherein the at least one donor-acceptor copolymer comprises phthalimide units and head-to-head substituted biheteroaryl units in an amount less than 1 mole percent.

10. The composition according to claim 9, wherein the at least one donor-acceptor copolymer comprises phthalimide units and head-to-head substituted biheteroaryl units in an amount less than 0.1 mole percent.

11. The composition according to claim 10, wherein the at least one donor-acceptor copolymer does not comprise phthalimide units and head-to-head substituted biheteroaryl units.

12. An ink composition comprising the composition according to claim 1.

13. The ink composition according to claim 12, wherein the ink comprises at least one halogenated solvent which is the majority solvent component by weight percentage.

14. The ink composition according to claim 12, wherein the ink comprises at least one non-halogenated solvent which is the majority solvent component by weight percentage.

15. The ink composition according to claim 12, wherein the ink comprises at least one non-halogenated aromatic solvent as the primary solvent.

16. The ink composition according to claim 12, wherein the ink comprises at least one halogenated solvent as the primary solvent.

17. The ink composition according to claim 12, wherein the ink comprises a solids content of about 1 wt. % to about 30 wt. %.

18. The ink composition according to claim 12, wherein the ink comprises a solids content of about 1.5 wt. % to about 5 wt. %.

19. The ink composition according to claim 12, wherein the ink further comprises at least one n-type material.

20. The ink composition according to claim 12, wherein the ink further comprises at least one n-type material which is a fullerene derivative.

21. The ink composition according to claim 12, wherein the ink further comprises at least one additive.

22. A coated substrate comprising at least one composition according to claim 1 disposed on a substrate.

23. The coated substrate of claim 22, wherein the coated substrate is part of an organic electronic device.

24. The coated substrate of claim 22, wherein the coated substrate is part of an organic electronic device which is an organic photovoltaic device.

25. The coated substrate of claim 22, wherein the coated substrate is part of an organic electronic device which is an organic photovoltaic device which provides a power conversion efficiency of at least 6%.

26. The coated substrate of claim 22, wherein the coated substrate is part of an organic electronic device which is an organic photovoltaic device which provides a power conversion efficiency of at least 7%.

27. The coated substrate of claim 22, wherein the coated substrate is part of an organic electronic device which is an organic photovoltaic device which provides a power conversion efficiency of at least 8%.

28. The coated substrate of claim 22, wherein the coated substrate is part of an organic electronic device which is an organic photovoltaic device which provides a power conversion efficiency of at least 6% and a Voc of at least 0.6 V.

29. The coated substrate of claim 22, wherein the coated substrate is part of an organic electronic device which is an organic photovoltaic device which provides a power conversion efficiency of at least 6% and a Voc of at least 0.7 V.

30. The coated substrate of claim 22, wherein the coated substrate is part of an organic electronic device which is an organic photovoltaic device which provides a power conversion efficiency of at least 6% and a Voc of at least 0.8 V.

31. The coated substrate of claim 22, wherein the coated substrate is part of an organic electronic device which is an organic photovoltaic device which provides a power conversion efficiency of at least 6% and a Voc of at least 1 V.

* * * * *